United States Patent
Gobbi et al.

(10) Patent No.: US 7,501,541 B2
(45) Date of Patent: Mar. 10, 2009

(54) MALONAMIDES AS OREXIN ANTAGONISTS

(75) Inventors: Luca Gobbi, Oberwil BL (CH); Henner Knust, Rheinfelden (DE); Parichehr Malherbe, Muttenz (CH); Matthias Nettekoven, Grenzach-Wyhlen (DE); Emmanuel Pinard, Linsdorf (FR); Olivier Roche, Folgensbourg (FR); Mark Rogers-Evans, Oberwil BL (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 12/044,002

(22) Filed: Mar. 7, 2008

(65) Prior Publication Data

US 2008/0249180 A1  Oct. 9, 2008

(30) Foreign Application Priority Data

Mar. 15, 2007  (EP)  .................. 07104232

(51) Int. Cl.
 C07C 233/05  (2006.01)
 A61K 31/65  (2006.01)
(52) U.S. Cl. .................. 564/156; 514/352; 514/354; 514/357; 514/451; 514/616; 546/309; 546/314; 546/328; 546/329; 549/424
(58) Field of Classification Search ............. 514/352, 514/354, 357, 451, 616; 546/309, 314, 328, 546/329; 549/424; 564/156
See application file for complete search history.

(56) References Cited

U.S. PATENT DOCUMENTS

| 3,529,012 A | 9/1970 | Loev et al. |
| 3,622,596 A * | 11/1971 | Fischer et al. ............. 548/312.7 |
| 4,322,418 A | 3/1982 | Loesel et al. |

FOREIGN PATENT DOCUMENTS

EP  1193248  4/2002

OTHER PUBLICATIONS

Siegel, J. M., Annu. Rev. Psychol. vol. 55, pp. 125-148 (2004).
De Lecea et al., Proc. Natl. Acad. Sci. USA vol. 95, pp. 322-327 (1998).
Sakurai et al., Cell, vol. 92, pp. 573-585 (1998).
Sakurai, Regulatory Peptides, vol. 126 pp. 3-10 (2005).
Peyron et al., J. Neurosci. vol. 18, pp. 9996-10015 (1998).
Nambu et al., Brain Res. vol. 827, pp. 243-260 (1999).
Chemelli et al., Cell, vol. 98 pp. 437-451 (1999).
Lin et al., Cell, vol. 98, pp. 365-376 (1999).
Nishino et al., Lancet, vol. 355, pp. 39-40 (2000).
Peyron et al., Nature Medicine vol. 6, pp. 991-997 (2000).
Mignot et al., Sleep vol. 11, pp. 1012-1020 (1997).
Piper et al., Eur. J. Neuroscience vol. 12, pp. 726-730 (2000).
Sakamoto et al., Regul. Pept. vol. 118, pp. 183-191 (2004).
Ida et al., Biochem. Biophys. Res. Comm. vol. 270, pp. 318-323 (2000).
Kuru et al., Neuroreport vol. 11 pp. 1977-1980 (2000).
Winsky-Sommerer et al., J. Neuroscience vol. 24 pp. 11439-11448 (2004).
Chang et al., Neuroscience Research vol. 57, Issue 3, pp. 462-466 (2007).
Suzuki et al., Brain Research vol. 1044 pp. 116-121 (2005).
Digby et al, J. Endocrinol. vol. 191 pp. 129-136 (2006).
Cai et al., Expert Opin. Ther. Patents, vol. 16(5) pp. 631-646 (2006).
Bingham et al., Current Opinion in Drug Discovery & Development vol. 9(5) pp. 551-559 (2006).
Bourgin et al., J. Neurosci. vol. 20(20), pp. 7760-7765 (2000).
Smith et al., Neurosci. Lett. vol. 341(3) pp. 256-258 (2003).
Malherbe et al., Mol. Pharmacol. vol. 64 pp. 823-832 (2003).
Database Beilstein, Beilstein Inst. for Org. Chem. XP0024807330.
Database Beilstein, Beilstein Inst. for Org. Chem. XP002480731.

* cited by examiner

*Primary Examiner*—Shailendra Kumar
(74) *Attorney, Agent, or Firm*—George W. Johnston; Patricia S. Rocha-Tramloni; Kimberly J. Prior

(57) ABSTRACT

The present invention relates to compounds of formula I

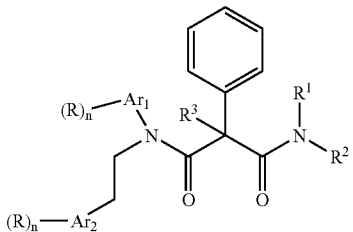

I wherein
$Ar_1$, $Ar_2$, R, $R^1$, $R^2$, $R^3$ and n are as defined herein
or to pharmaceutically suitable acid addition salts, optically pure enantiomers, racemates or diastereomeric mixtures thereof. Compounds of formula I are orexin receptor antagonists and may be useful in the treatment of disorders, in which orexin pathways are involved like sleep disorders.

23 Claims, No Drawings

MALONAMIDES AS OREXIN ANTAGONISTS

PRIORITY TO RELATED APPLICATION(S)

This application claims the benefit of European Patent Application No. 07104232.9, filed Mar. 15, 2007, which is hereby incorporated by reference in its entirety.

BACKGROUND OF THE INVENTION

Orexins (hypocretins), a family of hypothalamic neuropeptides, play an important role in modulating feeding behavior, energy homeostasis and the sleep-wake cycle (Siegel, *Annu. Rev. Psychol.*, 55, 125-148, 2004). The orexin-A/hypocretin1 (OX-A, 33 amino acids) and orexin-B/hypocretin2 (OX-B, 28 amino acids) are derived from the same precursor by proteolytic processing of 130 amino acids prepro-orexin (de Lecea et al., *Proc Natl Acad Sci USA*, 95, 322-327, 1998; Sakurai T. et al., *Cell*, 92, 573-585, 1998). The orexin levels show a diurnal variation being highest during the active cycle. Two receptor subtypes termed orexin-1 receptor ($OX_1R$) and orexin-2 receptor ($OX_2R$) have been identified. The characterization of both receptors in binding and functional assays demonstrated that $OX_2R$ is a non-selective receptor for both OX-A and -B, whereas $OX_1R$ is selective for OX-A, conversely OX-A is a non-selective neuropeptide and binds with similar affinities to $OX_1R$ and $OX_2R$, while OX-B is selective and has a higher affinity for OX2R (Sakurai T. et al., *Cell*, 92, 573-585, 1998). Both receptors belong to the class A family of G-protein-coupled receptors (GPCRs) that couple via $G_{q/11}$ to the activation of phospholipase C leading to phosphoinositide (PI) hydrolysis and elevation of intracellular $Ca^{2+}$ levels. However, it has been shown that OX2R could also couple via $G_{i/o}$ to cAMP pathway (Sakurai, *Regulatory Peptides*, 126, 3-10, 2005). Northern blot analysis of adult rat tissues showed that the prepro-orexin mRNA is detected exclusively in the brain (except for a small amount in the testis) and that the $OX_1R$ and $OX_2R$ transcripts are also exclusively detected in the brain (Sakurai T. et al., *Cell*, 92, 573-585, 1998). Similar results were obtained using human multiple tissue Northern blot. Distribution studies in rat brain using in situ hybridization and immunohistochemistry have shown that orexin neurons are found only in the lateral hypothalamic area with their projections to the entire CNS (Peyron et al., *J Neurosci*, 18, 9996-10015, 1998; Nambu et al., *Brain Res.*, 827, 243-60, 1999). In addition, both $OX_1$ and $OX_2$ receptors are present in brain regions important for the regulation of sleep/wakefulness.

A disrupted orexin system is suggested to be the cause of narcolepsy based on following lines of evidence: (a) Prepro-orexin knockout mice possessed a phenotype with characteristics remarkably similar to narcolepsy (Chemelli et al., *Cell*, 98, 437-451, 1999), (b) a mutation (canarc-1), which disrupts the gene encoding $OX_2R$, was found to be responsible for canine narcolepsy (Lin et al., *Cell*, 98, 365-376, 1999), (c) lack of OX-A and OX-B was observed in human narcoleptic patients (Nishino et al., *Lancet*, 355, 39-40, 2000; Peyron et al., *Nature Medicine*, 6, 991-997, 2000), (d) it has been shown that Modafinil, an anti-narcoleptic drug with unknown mechanism of action, activates orexin neurons (Mignot et al., *Sleep*, 11, 1012-1020, 1997; Chemelli et al., *Cell*, 98, 437-451, 1999). The intracerebroventricular (icv) administration of OX-A dose-dependently increases wakefulness in rat and also reduces total REM sleep by 84% (Piper et al., *Eur. J. Neuroscience*, 12, 726-730, 2000). Taken together, these observations are consistent with a crucial role of the orexin system in the modulation of sleep/wake cycle.

Orexin plays an important role in stress and anxiety via its interaction with the corticotropin-releasing factor (CRF) system in hypothalamus (Sakamoto et al., *Regul Pept.*, 118, 183-91, 2004). The icv injection of OX-A induces grooming (stress-response) which is blocked in part by a CRF antagonist (Ida et al., *Biochem. Biophys. Res. Comm.*, 270, 318-323, 2000). $OX_2R$ is highly expressed in adrenal medulla, whereas $OX_1R$ is high in adrenal cortex. Both OX-A and OX-B stimulate corticosterone release in plasma and induce c-Fos in paraventricular nucleus (PVN) in the hypothalamus (Kuru et al., *Neuroreport*, 11, 1977-1980, 2000). Furthermore, orexin neurons projecting to CRF neurons express mainly the $OX_2R$ (Winsky-Sommerer et al., *J. Neuroscience*, 24, 11439-11448, 2004). Therefore, OX2R stimulation activates the hypothalamo-pituitary-adrenal (HPA) axis. Interestingly, in this context, the orexin A-induced increases in plasma ACTH has been reported to be attenuated by a selective antagonist to OX-2R (N-{(1S)-1-(6,7-dimethoxy-3,4-dihydro-2(1H)-isoquinolinyl)carbonyl}-2,2-dimethylpropyl)-N-{4-pyridinylmethyl}amine (Chang et al., *Neurosci Res.*, 21 Dec. 2006). A recent preclinical report (Suzuki et al., *Brain Research*, 1044, 116-121, 2005) has suggested an anxiogenic effect of OX-A. The icv injection of OX-A caused an anxiety-like behavior in mice. Effects were similar to those of corticotropin-releasing factor (CRF) that was tested at the same time for comparison. A recent study has also demonstrated the presence of functional OX1 and OX2 receptors in human adipose tissue and their roles in adipose tissue metabolism and adipogenesis (Digby et al., *J. Endocrinol.*, 191, 129-36, 2006).

In summary, considering the very diverse functions played by orexin system in arousal, sleep/wakefulness, appetite regulation and their roles in anxiety and stress response, etc., one expects that the drugs (or compounds) targeting orexin system will have beneficial therapeutic effects for the treatments of diseases like sleep disorders including sleep apnea, narcolepsy, insomnia, parasomnia, jet lag syndrome, circadian rhythms disorder, restless leg syndrome, psychiatric, neurological and neurodegenerative disorders including anxiety, depression, manic depression, obsessive compulsive disorders, affective neurosis, depressive neurosis, anxiety neurosis, mood disorder, delirium, panic-attack disorder, posttraumatic stress disorders, sexual dysfunction, schizophrenia, psychosis, cognitive disorders, Alzheimer's and Parkinson's diseases, dementia, mental retardation, dyskinesias such as Huntington's disease and Tourette syndrome, addictions, craving associated with drug abuse, seizure disorders, epilepsy, metabolic diseases such as obesity, diabetes, eating disorders including anorexia and bulimia, asthma, migraine, pain, neuropathic pain, sleep disorders associated with psychiatric, neurological and neurodegenerative disorders, neuropathic pain, enhanced or exaggerated sensitivity to pain such as hyperalgesia, causalgia, and allodynia, acute pain, burn pain, back pain, complex regional pain syndrome I and II, arthritic pain, post-stroke pain, post-operative pain, neuralgia, pain associated with HIV infection, post-chemotherapy pain, irritable bowel syndrome and other diseases related to general orexin system dysfunction.

Numerous documents describe the current knowledge on orexin pathway, for example the following documents:

Expert Opin. Ther. Patents (2006), 16(5), 631-646

Current Opinion in Drug Discovery & Development, 2006, 9(5), 551-559

J. Neurosci (2000), 20(20), 7760-7765

Neurosci Lett, (2003), 341(3), 256-258

SUMMARY OF THE INVENTION

The present invention provides compounds of formula I

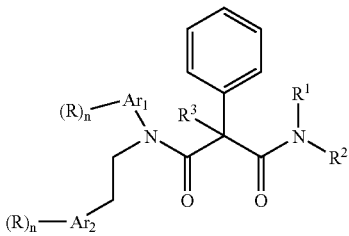

wherein $Ar_1$ and $Ar_2$ are each independently unsubstituted or substituted aryl or heteroaryl;

$R^1$ and $R^2$ are each independently hydrogen, lower alkyl, lower alkyl substituted by halogen, —$(CH_2)_o$—O-lower alkyl, —$(CH_2)_o$—N-(lower alkyl)$_2$, $(CH_2)_p$-cycloalkyl, $(CH_2)_p$-heterocycloalkyl, $(CH_2)_p$-aryl, or $(CH_2)_p$-heteroaryl, wherein cycloalkyl, heterocycloalkyl, aryl, and heteroaryl are optionally substituted by R, or $R^1$ and $R^2$ together with the N-atom to which they are attached form a heterocyclic ring, optionally containing further ring-heteroatoms selected from N, O and S, which ring is optionally substituted by R;

R is halogen, lower alkyl, lower alkyl substituted by halogen, lower alkoxy or lower alkoxy substituted by halogen;

$R^3$ is hydrogen or lower alkyl;

n is 0, 1, 2, 3 or 4;

o is 1, 2 or 3; and p is 0, 1 or 2;

or pharmaceutically suitable acid addition salts, optically pure enantiomers, racemates or diastereomeric mixtures thereof.

The compounds of formula I are novel. Their advantage over orexin receptor antagonists described in the literature is an improvement of physicochemical/DMPK profile which is an important aspect in the development as drug.

Compounds of formula I are orexin receptor antagonists and may be useful in the treatment of disorders in which orexin pathways are involved, like sleep disorders, including sleep apnea, narcolepsy, insomnia, parasomnia, jet lag syndrome, circadian rhythms disorder, and restless leg syndrome; psychiatric, neurological and neurodegenerative disorders, including anxiety, depression, manic depression, obsessive compulsive disorders, affective neurosis, depressive neurosis, anxiety neurosis, mood disorder, delirium, panic-attack disorder; posttraumatic stress disorders; sexual dysfunction; schizophrenia; psychosis; cognitive disorders; Alzheimer's and Parkinson's diseases; dementia; mental retardation; dyskinesias, such as Huntington's disease and Tourette syndrome; addictions; craving associated with drug abuse; seizure disorders; epilepsy; metabolic diseases such as obesity, diabetes, eating disorders including anorexia and bulimia; asthma; migraine; pain; neuropathic pain; sleep disorders associated with psychiatric, neurological and neurodegenerative disorders; neuropathic pain; enhanced or exaggerated sensitivity to pain such as hyperalgesia, causalgia, and allodynia; acute pain; burn pain; back pain; complex regional pain syndrome I and II; arthritic pain; post-stroke pain; post-operative pain; neuralgia; pain associated with HIV infection; post-chemotherapy pain; irritable bowel syndrome and other diseases related to general orexin system dysfunction.

DETAILED DESCRIPTION OF THE INVENTION

The following definitions of the general terms used in the present description apply irrespective of whether the terms in question appear alone or in combination. It must be noted that, as used in the specification and the appended claims, the singular forms "a", "an," and "the" include plural forms unless the context clearly dictates otherwise.

As used herein, the term "lower alkyl" denotes a straight- or branched-chain hydrocarbon group containing from 1-4 carbon atoms, for example, methyl, ethyl, propyl, isopropyl, n-butyl, i-butyl, t-butyl and the like. The term "alkyl" denotes a straight- or branched-chain hydrocarbon group containing from 1-7 carbon atoms.

The term "lower alkoxy" denotes a group containing an alkyl group as defined above, which is attached via an oxygen atom.

The term "halogen" denotes chlorine, iodine, fluorine and bromine.

The term "cycloalkyl" denotes a saturated carbocyclic group containing 3-6 carbon atoms.

The term "heterocycloalkyl" denotes a non aromatic cyclicradical incorporated one, two, or three ring heteroatoms selected from the group consisting of N, S, and O, for example oxetanyl, tetrahydrofuranyl, tetrahydropyranyl, azetidinyl; pyrrolidinyl, piperidinyl, piperazinyl, morpholinyl, thiomorpholinyl or di-oxothiomorpholinyl.

The term "aryl" means the monovalent cyclic aromatic hydrocarbon group consisting of one or more fused rings in which at least one ring is aromatic in nature. Examples of aryl radicals include, but are not limited to, phenyl, naphthyl, biphenyl, indanyl, anthraquinolyl, and the like.

"Heteroaryl" means the monovalent aromatic cyclic group having one or more rings in which at least one ring is aromatic in nature, incorporating one, two, or three ring heteroatoms (chosen from nitrogen, oxygen, or sulfur). Examples of heteroaryl radicals include, but are not limited to, imidazolyl, oxazolyl, isoxazolyl, thiazolyl, thiophenyl, furanyl, pyridinyl, pyrazinyl, pyrimidinyl, pyridazinyl, quinolinyl, isoquinolinyl, benzofuryl, benzothiophenyl, benzothiopyranyl, benzimidazolyl, benzooxazolyl, benzothiazolyl, benzopyranyl, indazolyl, indolyl, isoindolyl, naphtyridinyl, benzo[1,3]dioxolyl, 2,3-dihydro-benzo[1,4]dioxinyl and the like.

The term "heterocyclic ring, optionally containing further ring-heteroatoms selected from N, O and S" means a non-aromatic ring containing one N-atom, and optionally containing one or more heteroatom replaced by O, N or S, for example pyrrolin-1-yl, piperidin-1-yl, azepin-1-yl, piperazin-1-yl, morpholin-4-yl, thiomorpholin-4-yl, 1-oxo-thiomorpholin-4-yl or 1,1-dioxo-thiomorpholin-4-yl.

As used herein, the term "lower alkyl substituted by halogen" denotes an alkyl group as defined above, wherein at least one hydrogen atom is replaced by halogen, for example $CF_3$, $CHF_2$, $CH_2F$, $CH_2CF_3$, $CH_2CH_2CF_3$, $CH_2CF_2CF_3$ and the like.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methanesulfonic acid, p-toluenesulfonic acid and the like.

"Therapeutically effective amount" means an amount that is effective to prevent, alleviate or ameliorate symptoms of disease or prolong the survival of the subject being treated.

Preferred compounds of formula I are those of formula I-1

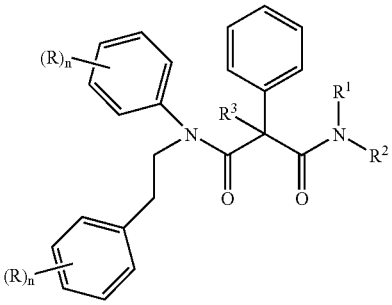

I-1 wherein
$R^1$ and $R^2$ are each independently hydrogen, lower alkyl, lower alkyl substituted by halogen, —$(CH_2)_o$—O-lower alkyl, —$(CH_2)_o$—N-(lower alkyl)$_2$, $(CH_2)_p$-cycloalkyl, $(CH_2)_p$-heterocycloalkyl, $(CH_2)_p$-aryl, or $(CH_2)_p$-heteroaryl, wherein the cycloalkyl, heterocycloalkyl, aryl, and heteroaryl rings are optionally substituted by R, or $R^1$ and $R^2$ together with the N-atom to which they are attached form a heterocyclic ring, optionally containing further ring-heteroatoms selected from N, O and S, which ring is optionally substituted by R;

R is halogen, lower alkyl, lower alkyl substituted by halogen, lower alkoxy or lower alkoxy substituted by halogen;

$R^3$ is hydrogen or lower alkyl;

n is 0, 1, 2, 3 or 4;

o is 1, 2 or 3; and p is 0, 1 or 2;

or pharmaceutically suitable acid addition salts, optically pure enantiomers, racemates or diastereomeric mixtures thereof.

Examples of preferred compounds of formula I-1 are the following compounds:

N-(4-chloro-3-methoxy-phenyl)-N',N'-dimethyl-2-phenyl-N-[2-(4-trifluoromethyl-phenyl)-ethyl]-malonamide and N-(3-chloro-4-methoxy-phenyl)-N',N'-dimethyl-2-phenyl-N-[2-(4-trifluoromethyl-phenyl)-ethyl]-malonamide.

Preferred compounds of formula I-1 are further those of formula I-2

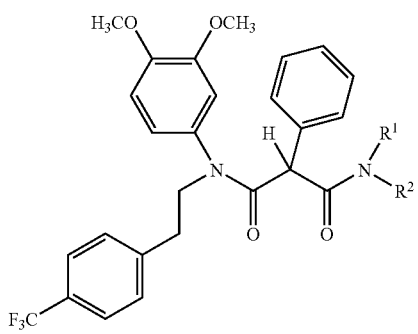

I-2 wherein
$R^1$ and $R^2$ are each independently hydrogen, lower alkyl, lower alkyl substituted by halogen, —$(CH_2)_o$—O-lower alkyl, —$(CH_2)_o$—N-(lower alkyl)$_2$, $(CH_2)_p$-cycloalkyl, $(CH_2)_p$-heterocycloalkyl, $(CH_2)_p$-aryl, $(CH_2)_p$-heteroaryl, wherein cycloalkyl, heterocycloalkyl, aryl, and heteroaryl are optionally substituted by R, or $R^1$ and $R^2$ together with the N-atom to which they are attached form a heterocyclic ring, optionally containing further ring-heteroatoms selected from N, O and S, which ring is optionally substituted by R;

R is halogen, lower alkyl, lower alkyl substituted by halogen, lower alkoxy or lower alkoxy substituted by halogen;

o is 1, 2 or 3; and p is 0, 1 or 2;

or pharmaceutically suitable acid addition salts, optically pure enantiomers, racemates or diastereomeric mixtures thereof.

Preferred compounds from formula I-2 are those, wherein one of $R^1$ or $R^2$ is hydrogen and the other is lower alkyl, for example N-(3,4-dimethoxy-phenyl)-N'-methyl-2-phenyl-N-[2-(4-trifluoromethyl-phenyl)-ethyl]-malonamide N-butyl-N'-(3,4-dimethoxy-phenyl)-2-phenyl-N'-[2-(4-trifluoromethyl-phenyl)-ethyl]-malonamide N-(3,4-dimethoxy-phenyl)-N'-ethyl-2-phenyl-N-[2-(4-trifluoromethyl-phenyl)-ethyl]-malonamide and N-(3,4-dimethoxy-phenyl)-2-phenyl-N'-propyl-N-[2-(4-trifluoromethyl-phenyl)-ethyl]-malonamide.

Further preferred are compounds, wherein one of $R^1$ or $R^2$ is hydrogen and the other is —$(CH_2)_o$—O-lower alkyl, for example N-(3,4-dimethoxy-phenyl)-N'-(2-methoxy-ethyl)-2-phenyl-N-[2-(4-trifluoromethyl-phenyl)-ethyl]-malonamide.

Further preferred are compounds, wherein one of $R^1$ or $R^2$ is hydrogen and the other is phenyl substituted by halogen, for example N-(3,4-dimethoxy-phenyl)-N'-(4-fluoro-phenyl)-2-phenyl-N-[2-(4-trifluoromethyl-phenyl)-ethyl]-malonamide.

Further preferred are compounds, wherein $R^1$ and $R^2$ are both hydrogen, for example N-(3,4-dimethoxy-phenyl)-2-phenyl-N-[2-(4-trifluoromethyl-phenyl)-ethyl]-malonamide.

Further preferred are compounds, wherein $R^2$ is unsubstituted or substituted $(CH_2)_p$-aryl, for example N-(3,4-dimethoxy-phenyl)-N'-(4-methyl-benzyl)-2-phenyl-N-[2-(4-trifluoromethyl-phenyl)-ethyl]-malonamide N-(3,4-dimethoxy-phenyl)-N'-methyl-N'-phenethyl-2-phenyl-N-[2-(4-trifluoromethyl-phenyl)-ethyl]-malonamide and N-benzyl-N'-(3,4-dimethoxy-phenyl)-N-methyl-2-phenyl-N'-[2-(4-trifluoromethyl-phenyl)-ethyl]-malonamide.

Further preferred are compounds, wherein one of $R^1$ or $R^2$ is hydrogen and the other is unsubstituted or substituted $(CH_2)_p$-cycloalkyl, for example N-cyclopropyl-N'-(3,4-dimethoxy-phenyl)-2-phenyl-N'-[2-(4-trifluoromethyl-phenyl)-ethyl]-malonamide and N-cyclopropylmethyl-N'-(3,4-dimethoxy-phenyl)-2-phenyl-N'-[2-(4-trifluoromethyl-phenyl)-ethyl]-malonamide.

Further preferred are compounds, wherein one of $R^1$ or $R^2$ is hydrogen and the other is lower alkyl substituted by halogen, for example N-(2,2-difluoro-ethyl)-N'-(3,4-dimethoxy-phenyl)-2-phenyl-N'-[2-(4-trifluoromethyl-phenyl)-ethyl]-malonamide.

Further preferred are compounds, wherein one of $R^1$ or $R^2$ is hydrogen and the other is unsubstituted or substituted $(CH_2)_p$-heteroaryl, for example N-(3,4-dimethoxy-phenyl)-2-phenyl-N'-pyridin-3-yl-N-[2-(4-trifluoromethyl-phenyl)-ethyl]-malonamide and N-(3,4-dimethoxy-phenyl)-2-phenyl-N'-pyridin-3-ylmethyl-N-[2-(4-trifluoromethyl-phenyl)-ethyl]-malonamide.

Further preferred are compounds, wherein one of $R^1$ or $R^2$ is hydrogen and the other is unsubstituted or substituted $(CH_2)_p$-heterocycloalkyl, for example N-(3,4-dimethoxy-phenyl)-2-phenyl-N'-(tetrahydro-pyran-4-yl)-N-[2-(4-trifluoromethyl-phenyl)-ethyl]-malonamide.

One embodiment of the present invention relates to compounds of formula

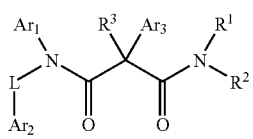

I wherein $Ar_1$ and $Ar_2$ are unsubstituted or substituted aryl or heteroaryl and wherein the aryl and the heteroaryl groups are optionally substituted by one or more substituents selected from the group consisting of hydroxy, halogen, lower alkyl, lower alkyl substituted by halogen, lower alkoxy, lower alkoxy substituted by halogen, nitro, cyano, $SO_2$-lower alkyl and $-NR^1R^2$;

$Ar_3$ is unsubstituted or substituted aryl or heteroaryl and wherein the aryl and the heteroaryl groups are optionally substituted by one or more substituents selected from the group consisting of halogen, lower alkyl, lower alkyl substituted by halogen, lower alkoxy, and lower alkoxy substituted by halogen;

$R^1$ and $R^2$ are each independently hydrogen, lower alkyl, lower alkyl substituted by halogen, $-(CH_2)_o$-O-lower alkyl, $-(CH_2)_o$-N-(lower alkyl)$_2$, $(CH_2)_p$-cycloalkyl, $(CH_2)_p$-heterocycloalkyl, $(CH_2)_p$-aryl, or $(CH_2)_p$-heteroaryl, wherein cycloalkyl, heterocycloalkyl, aryl, or heteroaryl are optionally substituted by R, or $R^1$ and $R^2$ together with the N-atom to which they are attached form a heterocyclic ring, optionally containing further ring-heteroatoms selected from N, O and S, which ring is optionally substituted by R;

R is lower alkyl, lower alkoxy, halogen or lower alkyl substituted by halogen;

$R^3$ is hydrogen, lower alkyl or halogen;

L is $-(CR^4R^5)_n-$;

$R^4$ and $R^5$ are each independently hydrogen or lower alkyl;

n is 0, 1, 2 or 3;

o is 2 or 3; and p is 0, 1 or 2;

or pharmaceutically suitable acid addition salts, optically pure enantiomers, racemates or diastereomeric mixtures thereof.

The present compounds of formula I and their pharmaceutically acceptable salts can be prepared by methods known in the art, for example, by processes described below, which process comprises cleaving off the ester group in a compound of formula

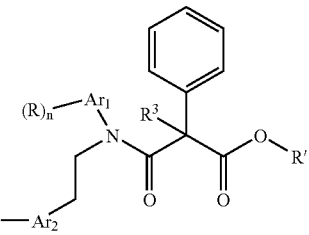

VI wherein R' is lower alkyl or benzyl under aqueous basic conditions and converting the corresponding acid with an amine of formula $NHR^1R^2$ under coupling conditions to obtain the malonamide of formula

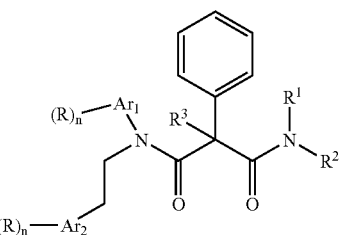

I wherein the substituents are as described above, and if desired, converting the compounds obtained into pharmaceutically acceptable acid addition salts.

The preparation of compounds of formula I of the present invention can be carried out in sequential or convergent synthetic routes. Syntheses of the compounds of the invention are shown in the following scheme. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in scheme 1, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

Scheme 1

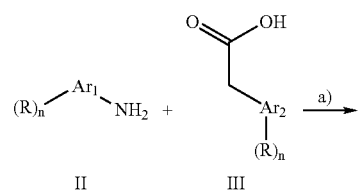

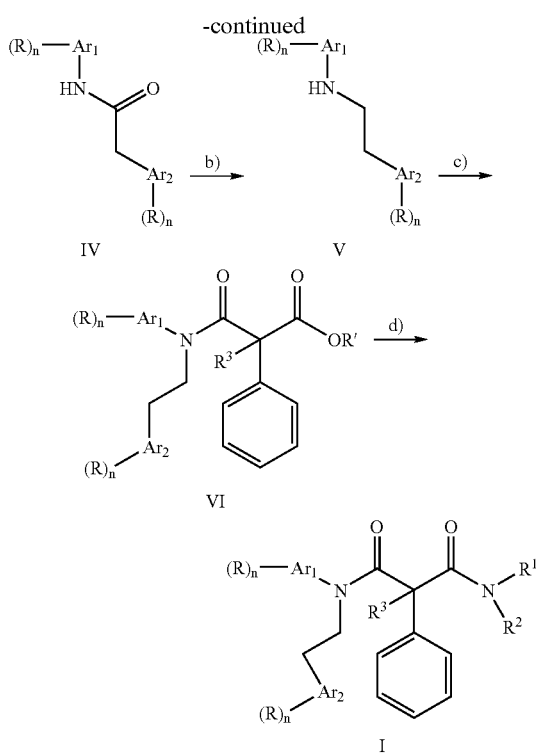

The substituents are as described above and R' is lower alkyl or benzyl.

a) Aryl amine derivatives II and arylacetic acid derivatives III are commercially available or can be accessed by methods described in literature. Reaction of aryl amine derivatives II with arylacetic acid derivatives III can be achieved by various methods as described in literature (for reaction conditions described in literature affecting such reactions see for example: Comprehensive Organic Transformations: A Guide to Functional Group Preparations, 2nd Edition, Richard C. Larock. John Wiley & Sons, New York, N.Y. 1999). However, it is convenient to react aryl amine derivative II with aryl acetic acid derivative III in the presence of a coupling reagent, a base and a solvent. For example coupling reagents like N,N'-carbonyldiimidazole (CDI), N,N'-dicyclohexylcarbodiimide (DCC), 1-(3-dimethylaminopropyl)-3-ethylcarbodiimide hydrochloride (EDCI), 1-[bis(dimethylamino)methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyluronium tetrafluoroborate (TBTU) and the like can equally well be employed to affect such transformation. We find it convenient to carry out the reaction in a solvent like dimethylformamide (DMF) and in the presence of a base. There is no particular restriction on the nature of the solvent to be employed, provided that it has no adverse effect on the reaction or the reagents involved and that it can dissolve the reagents, at least to some extent. Examples for suitable solvents include: DMF, dichloromethane (DCM), dioxane, THF, and the like. There is no particular restriction on the nature of the base used in this stage, and any base commonly used in this type of reaction may equally be employed here. Examples of such bases include triethylamine and diisopropylethylamine, and the like. The reaction can take place over a wide range of temperatures, and the precise reaction temperature is not critical to the invention. We find it convenient to carry out the reaction with heating from ambient temperature to reflux. The time required for the reaction can also vary widely, depending on many factors, notably the reaction temperature and the nature of the reagents. However, a period of from 0.5 h to several days will usually suffice to yield amide derivatives IV.

b) Reduction of the amide derivatives IV to the corresponding amine derivatives V can be achieved by various methods as described in literature. However, it is convenient to react amide derivative IV with a reducing agent in the presence of a solvent. For example lithium aluminum hydride (LiAlH$_4$) or borane (BH$_3$) and the like can equally well be employed to affect such transformation. We find it convenient to carry out the reaction in a solvent like tetrahydrofuran (THF). There is no particular restriction on the nature of the solvent to be employed, provided that it has no adverse effect on the reaction or the reagents involved and that it can dissolve the reagents, at least to some extent. The reaction can take place over a wide range of temperatures, and the precise reaction temperature is not critical to the invention. We find it convenient to carry out the reaction with heating from ambient temperature to reflux. The time required for the reaction can also vary widely, depending on many factors, notably the reaction temperature and the nature of the reagents. However, a period of from 0.5 h to several days will usually suffice to yield amine derivatives V.

Amine derivatives V can be reacted with malonic acid derivatives to form ester derivatives VI under various conditions. For reaction conditions described in literature affecting such or similar reactions see for example: Comprehensive Organic Transformations: A Guide to Functional Group Preparations, 2nd Edition, Richard C. Larock. John Wiley & Sons, New York, N.Y. 1999). Malonic acid derivatives are either commercially available or can be prepared from commercially available starting materials. Malonic acid derivatives $R^3$=H can be derivatised to access malonic acid derivatives in which $R^3$=alkyl, halogen by reacting malonic acid derivatives $R^3$=H with electrophiles ($R^3$—X; X=leaving group) in the presence of a base or and a solvent. Nevertheless, it is convenient to react amine derivative V with protected phenyl malonic acid derivatives (R'=ethyl, benzyl and the like), pre-activated through transformation into the respective acid chloride, or by employing an coupling reagent during the course of the reaction. This can be done in a solvent in the presence of a base. For example coupling reagents like N,N'-carbonyldiimidazole (CDI), N,N'-dicyclohexylcarbodiimide (DCC), 1-(3-dimethylaminopropyl)-3-ethylcarbodiimide hydrochloride (EDCI), 1-[bis(dimethylamino)methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyluronium tetrafluoroborate (TBTU) and the like can equally well be employed to affect such transformation. We find it convenient to carry out the reaction in a solvent like dimethylformamide (DMF) or dichloromethane (DCM) and in the presence of a base. There is no particular restriction on the nature of the solvent to be employed, provided that it has no adverse effect on the reaction or the reagents involved and that it can dissolve the reagents, at least to some extent. Examples for other suitable solvents include: dioxane, THF, and the like. There is no particular restriction on the nature of the base used in this stage, and any base commonly used in this type of reaction may equally be employed here. Examples of such bases include triethylamine and diisopropylethylamine, and the like. The reaction can take place over a wide range of temperatures, and the precise reaction temperature is not critical to the invention. We find it convenient to carry out the reaction with heating from ambient temperature to reflux. The time required for the reaction can also vary widely, depending on many factors, notably the reaction temperature and the nature of the reagents. However, a period of from 0.5 h to several days will usually suffice to yield ester derivatives VI.

Transformation of ester derivative VI into the final malonamide derivatives can be done according to procedures described in literature. However, we find it convenient to employ a two step reaction sequence in which the ester functionality in VI is cleaved under aqueous basic conditions (R'=Et) or reductively (R'=benzyl) with $H_2$ and Pd/C and the liberated acid functionality converted with the respective amines under coupling conditions and to the malonamide derivatives I. The coupling of carboxylic acids with amines is widely described in literature and the procedures are known to those in the art (For reaction conditions described in literature affecting such reactions see for example: Comprehensive Organic Transformations: A Guide to Functional Group Preparations, 2nd Edition, Richard C. Larock. John Wiley & Sons, New York, N.Y. 1999). The intermediately built acid can conveniently be transformed to the respective amide through coupling with an amine (either commercially available or accessible by methods described in references or by methods known in the art; as appropriate) by employing the usage of coupling reagents. For example coupling reagents like N,N'-carbonyldiimidazole (CDI), N,N'-dicyclohexylcarbodiimide (DCC), 1-(3-dimethylaminopropyl)-3-ethylcarbodiimide hydrochloride (EDCI), 1-[bis(dimethylamino)methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyluronium tetrafluoroborate (TBTU) and the like can equally well be employed to affect such transformation. We find it convenient to carry out the reaction in a solvent like dimethylformamide (DMF) and in the presence of a base. There is no particular restriction on the nature of the solvent to be employed, provided that it has no adverse effect on the reaction or the reagents involved and that it can dissolve the reagents, at least to some extent. Examples for suitable solvents include: DMF, dichloromethane (DCM), dioxane, THF, and the like. There is no particular restriction on the nature of the base used in this stage, and any base commonly used in this type of reaction may equally be employed here. Examples of such bases include triethylamine and diisopropylethylamine, and the like. The reaction can take place over a wide range of temperatures, and the precise reaction temperature is not critical to the invention. We find it convenient to carry out the reaction with heating from ambient temperature to reflux. The time required for the reaction can also vary widely, depending on many factors, notably the reaction temperature and the nature of the reagents. However, a period of from 0.5 h to several days will usually suffice to yield malonamide derivatives I.

The compounds were investigated in accordance with the test given hereinafter.

Intracellular $Ca^{2+}$ Mobilization Assay

The Chinese Hamster Ovary (dHFr-) mutant cell line stably expressing human orexin-1 (hOX1) or human orexin-2 (hOX2) receptors were maintained in Dulbecco's Modified Eagle Medium (1X) with GlutaMax™ 1, 4500 mg/L D-Glucose and Sodium Pyruvate (Catalog No. 31966-021, Invitrogen, Carlsbad, Calif.), 5% dialyzed fetal calf serum (Catalog No. 26400-044), 100 μg/ml penicillin and 100 μg/ml streptomycin. The cells were seeded at $5 \times 10^4$ cells/well in the poly-D-lysine treated, 96-well, black/clear-bottomed plates (Catalog No. BD356640, BD Biosciences, Palo Alto, Calif.). 24 h later, the cells were loaded for 1 h at 37° C. with 4 μM Flou-4 acetoxymethyl ester (Catalog No. F-14202, Molecular Probes, Eugene, Oreg.) in FLIPR buffer (1×HBSS, 20 mM HEPES, 2.5 mM Probenecid). Hanks' Balanced Salt Solution (HBSS) (10×) (catalog No. 14065-049) and HEPES (1M) (catalog No. 15630-056) were purchased from Invitrogen, Carlsbad, Calif. Probenecid (250 mM) (catalog No. P8761) was from Sigma, Buchs, Switzerland. The cells were washed five times with FLIPR buffer to remove excess dye and intracellular calcium mobilization, $[Ca^{2+}]_i$ were measured using a Fluorometric Imaging Plate Reader (FLIPR-96, Molecular Devices, Menlo Park, Calif.) as described previously (Malherbe et al., Mol. Pharmacol., 64, 823-832, 2003). Orexin A (catalog No. 1455, Toris Cookson Ltd, Bristol, UK) was used as agonist. Orexin A (50 mM stock solution in DMSO) was diluted in FLIPR buffer +0.1% BSA. The $EC_{50}$ and $EC_{80}$ values of orexin-A were measured daily from standard agonist concentration-response curves in CHO(dHFr-)-OX1R and -OX2R cell lines. All compounds were dissolved in 100% DMSO. Inhibition curves were determined by addition of 11 concentrations (0.0001-10 μM) of inhibitory compounds and using $EC_{80}$ value of orexin-A as agonist (a concentration which gave 80% of max agonist response, determined daily). The antagonists were applied 25 min (incubation at 37° C.) before the application of the agonist. Responses were measured as peak increase in fluorescence minus basal, normalized to the maximal stimulatory effect induced by $EC_{80}$ value of orexin-A or orexin-B. Inhibition curves were fitted according to the Hill equation: $y=100/(1+(x/IC_{50})^{n_H})$, where $n_H$=slope factor using Excel-fit 4 software (Microsoft). $K_b$ values were calculated according to the following equation $K_b=IC_{50}/(1+[A]/EC_{50})$ where A is the concentration of agonist added which is very close to agonist $EC_{80}$ value, and $IC_{50}$ and EC50 values were derived from the antagonist inhibition and orexin-A or B agonist curves, respectively.

Representative compounds show a $K_b$ value (μM) in human on orexin receptor as shown in the table below.

| Example | $K_b$ (μM) OX2R (human) | $K_b$ (μM) OX1R (human) |
| --- | --- | --- |
| 1 | 0.0255 | 0.1604 |
| 2 | 0.0172 | 0.1273 |
| 3 | 0.0419 | — |
| 5 | 0.0217 | 0.2287 |
| 13 | 0.0968 | 0.2182 |
| 14 | 0.0141 | 0.2338 |
| 15 | 0.0428 | 0.1662 |
| 16 | 0.0817 | 0.2517 |
| 17 | 0.0299 | 0.1908 |
| 18 | 0.0197 | 0.1993 |
| 19 | 0.0523 | 0.245 |
| 20 | 0.0468 | 0.2924 |
| 21 | 0.0278 | 0.173 |
| 22 | 0.0838 | 0.4395 |
| 23 | 0.023 | 0.2382 |
| 24 | 0.2447 | 0.2447 |
| 56 | 0.055 | 0.2948 |
| 58 | 0.0572 | 0.7229 |

The present invention also provides pharmaceutical compositions containing one or more compounds of formula I or a pharmaceutically acceptable salt thereof and a pharmaceutically acceptable carrier. These pharmaceutical compositions can be in the form of tablets, coated tablets, dragées, hard and soft gelatin capsules, solutions, emulsions, suspensions, suppositories or injectable solutions. They can be administered orally, rectally or parenterally.

In addition to a compound of formula I or a pharmaceutically acceptable salt thereof, compositions of the invention contain a pharmaceutically acceptable carrier. Suitable pharmaceutically acceptable carriers are pharmaceutically inert, inorganic or organic carriers. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The invention also provides a method for preparing compositions of the invention which comprises bringing one or more compounds of formula I and/or pharmaceutically acceptable acid addition salts thereof and, if desired, one or more other therapeutically valuable substances into a galenical administration form together with one or more therapeutically inert carriers.

The most preferred indications in accordance with the present invention are those, which include sleep disorders including sleep apnea, narcolepsy, insomnia, parasomnia, jet lag syndrome, circadian rhythms disorder, restless leg syndrome, psychiatric, neurological and neurodegenerative disorders including anxiety, depression, manic depression, obsessive compulsive disorders, affective neurosis, depressive neurosis, anxiety neurosis, mood disorder, delirium, panic-attack disorder, posttraumatic stress disorders, sexual dysfunction, schizophrenia, psychosis, cognitive disorders, Alzheimer's and Parkinson's diseases, dementia, mental retardation, dyskinesias such as Huntington's disease and Tourette syndrome, addictions, craving associated with drug abuse, seizure disorders, epilepsy, metabolic diseases such as obesity, diabetes, eating disorders including anorexia and bulimia, asthma, migraine, pain, neuropathic pain, sleep disorders associated with psychiatric, neurological and neurodegenerative disorders, neuropathic pain, enhanced or exaggerated sensitivity to pain such as hyperalgesia, causalgia, and allodynia, acute pain, burn pain, back pain, complex regional pain syndrome I and II, arthritic pain, post-stroke pain, post-operative pain, neuralgia, pain associated with HIV infection, post-chemotherapy pain, irritable bowel syndrome and other diseases related to general orexin system dysfunction.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage can be administered as single dose or in divided doses and, in addition, the upper limit can also be exceeded when this is found to be indicated.

Tablet Formulation (Wet Granulation)

|      |                         | mg/tablet |       |        |        |
|------|-------------------------|-----------|-------|--------|--------|
| Item | Ingredients             | 5 mg      | 25 mg | 100 mg | 500 mg |
| 1.   | Compound of formula I   | 5         | 25    | 100    | 500    |
| 2.   | Lactose Anhydrous DTG   | 125       | 105   | 30     | 150    |
| 3.   | Sta-Rx 1500             | 6         | 6     | 6      | 30     |
| 4.   | Microcrystalline Cellulose | 30     | 30    | 30     | 150    |
| 5.   | Magnesium Stearate      | 1         | 1     | 1      | 1      |
|      | Total                   | 167       | 167   | 167    | 831    |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

|      |                         | mg/capsule |       |        |        |
|------|-------------------------|------------|-------|--------|--------|
| Item | Ingredients             | 5 mg       | 25 mg | 100 mg | 500 mg |
| 1.   | Compound of formula I   | 5          | 25    | 100    | 500    |
| 2.   | Hydrous Lactose         | 159        | 123   | 148    | —      |
| 3.   | Corn Starch             | 25         | 35    | 40     | 70     |
| 4.   | Talc                    | 10         | 15    | 10     | 25     |
| 5.   | Magnesium Stearate      | 1          | 2     | 2      | 5      |
|      | Total                   | 200        | 200   | 300    | 600    |

Manufacturing Procedure
1. Mix items 1, 2 and 3 in a suitable mixer for 30 minutes.
2. Add items 4 and 5 and mix for 3 minutes.
3. Fill into a suitable capsule.

EXAMPLE 1

N-(3,4-Dimethoxy-phenyl)-N'-methyl-2-phenyl-N-[2-(4-trifluoromethyl-phenyl)-ethyl]-malonamide

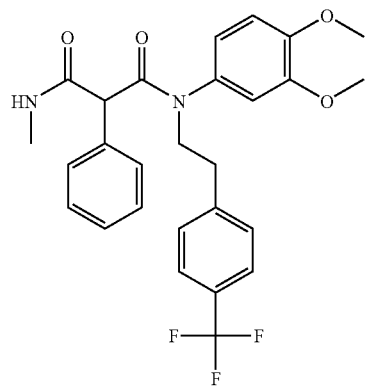

a) Step 1:

N-(3,4-Dimethoxy-phenyl)-2-(4-trifluoromethyl-phenyl)-acetamide

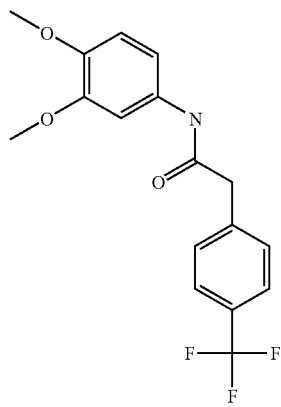

A mixture of 4 g (26 mmol) 3,4-dimethoxy-phenylamine (commercially available), 5.88 g (29 mmol) (4-trifluoro-phenyl)-acetic acid (commercially available), 10 g (31 mmol) TBTU and 5.28 g (52 mmol) NEt₃ in 15 mL DMF was stirred at room temperature for 30 minutes. All volatiles were removed under reduced pressure and the residue was taken up in DCM and 1M HCl aq. The organic phase was dried with MgSO₄ and evaporated to dryness. The residue was titurated with DCM and ethyl acetate to yield after drying 7.88 g (89%) of the title compound. MS(m/e): 340.3 (MH⁺).

b) Step 2:

(3,4-Dimethoxy-phenyl)-[2-(4-trifluoromethyl-phenyl)-ethyl]-amine (intermediate 1)

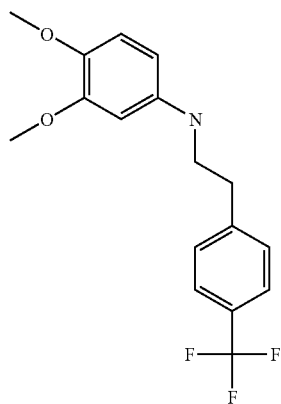

A mixture of 3 g (8.8 mmol) N-(3,4-Dimethoxy-phenyl)-2-(4-trifluoromethyl-phenyl)-acetamide and 1 g (26.3 mmol) LiAlH₄ in 100 mL THF was stirred for 1 h at room temperature. Water and HCl aq. was added and the mixture was extracted with ethyl acetate. The combined organic phases were washed with water, dried with MgSO₄ and evaporated to dryness. The residue was purified by flash column chromatography on silica eluting with a gradient formed from ethyl acetate and heptane. The product containing fractions were combined and evaporated to dryness to yield 0.7 g (24%) of the title compound. MS(m/e): 326.1 (MH⁺).

c) Step 3:

N-(3,4-Dimethoxy-phenyl)-2-phenyl-N-[2-(4-trifluoromethyl-phenyl)-ethyl]-malonamic acid benzyl ester

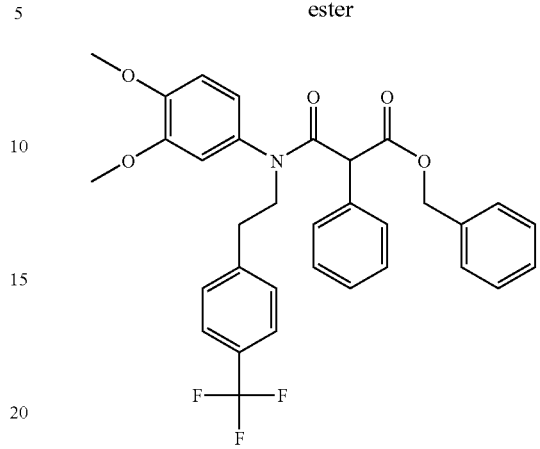

A mixture of 0.7 g (2.1 mmol) (3,4-Dimethoxy-phenyl)-[2-(4-trifluoromethyl-phenyl)-ethyl]-amine, 0.58 g (2.1 mmol) 2-phenyl-malonic acid monobenzylester (commercially available), 0.83 g (2.5 mmol) TBTU and 0.43 g (4.3 mmol) NEt₃ in 15 mL DMF was stirred at room temperature for 16 h. After evaporation to dryness the residue was treated with HCl aq. and DCM. The combined organic phases were washed with HCl aq., dried with MgSO4 and evaporated to dryness. The residue was purified by flash column chromatography on silica eluting with a gradient formed from ethyl acetate and heptane. The product containing fractions were combined and evaporated to dryness to yield 0.35 g (29%) of the title compound. MS(m/e): 578.3 (MH⁺).

d) Step 4:

N-(3,4-Dimethoxy-phenyl)-2-phenyl-N-[2-(4-trifluoromethyl-phenyl)-ethyl]-malonamic acid

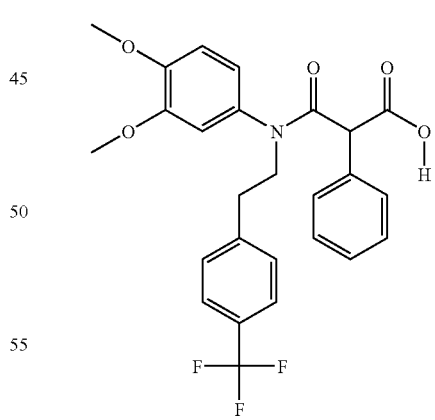

0.35 g (0.62 mmol) N-(3,4-Dimethoxy-phenyl)-2-phenyl-N-[2-(4-trifluoromethyl-phenyl)-ethyl]-malonamic acid benzyl ester in 20 mL ethyl acetate and 0.37 mL acetic acid was hydrogenated over Pd/C with atmospheric pressure of H₂ for 16 h at room temperature. The catalyst was filtered off and the and the filtrate evaporated to dryness. The acid was used without further purification in the consecutive step. MS(m/e): 488.2 (MH⁺).

e) Step 5:

N-(3,4-Dimethoxy-phenyl)-N'-methyl-2-phenyl-N-[2-(4-trifluoromethyl-phenyl)-ethyl]-malonamide

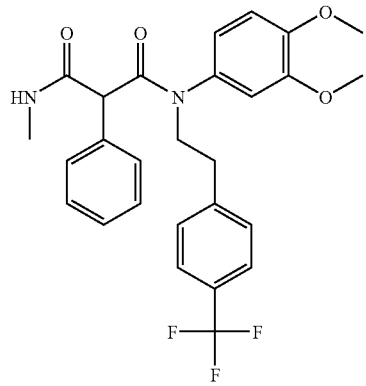

A mixture of 16.2 mg (0.033 mmol) N-(3,4-Dimethoxy-phenyl)-2-phenyl-N-[2-(4-trifluoromethyl-phenyl)-ethyl]-malonamic acid, 15.5 mg (0.049 mmol) methylamine (commercially available), 13.8 mg (0.043 mmol) TBTU and 7.8 mg (0.09 mmol) pyridine in 2 mL DMF was shaken for 4 h at room temperature. The mixture was evaporated to dryness, taken up in methanol, formic acid and subjected to purification by preparative HPLC on reversed phase eluting with a gradient formed from acetonitrile, water and acetic acid. The combined product fractions were evaporated to dryness to yield 2.7 mg (16%) of the title compound. MS(m/e): 501.3 (MH$^+$), MH$^+$ found: 501.3.

In analogy to the procedure described for the synthesis of example 1 further malonamide derivatives have been synthesized from their respective starting materials mentioned in table 1.

The examples are shown in table 1 and comprise example 2-example 27.

TABLE 1

| No | structure | MW | name | starting material | MW MH+ found |
|----|-----------|-----|------|-------------------|--------------|
| 2  | 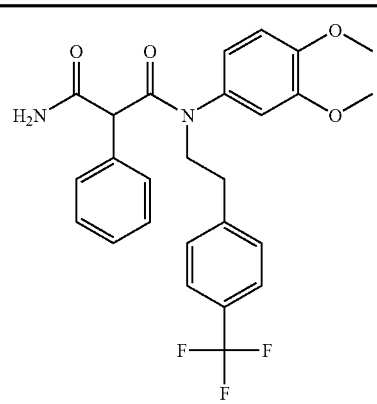          | 486.5 | N-(3,4-Dimethoxy-phenyl)-2-phenyl-N-[2-(4-trifluoromethyl-phenyl)-ethyl]-malonamide | N-(3,4-Dimethoxy-phenyl)-2-phenyl-N-[2-(4-trifluoromethyl-phenyl)-ethyl]-malonamic acid and ammonia (commercially available) | 487.3 |
| 3  | 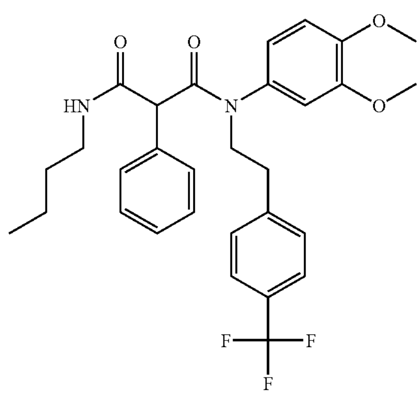          | 542.6 | N-Butyl-N'-(3,4-dimethoxy-phenyl)-2-phenyl-N'-[2-(4-trifluoromethyl-phenyl)-ethyl]-malonamide | N-(3,4-Dimethoxy-phenyl)-2-phenyl-N-[2-(4-trifluoromethyl-phenyl)-ethyl]-malonamic acid and n-butylamine (commercially available) | 543.4 |

TABLE 1-continued

| No | structure | MW | name | starting material | MW MH+ found |
|---|---|---|---|---|---|
| 4 | 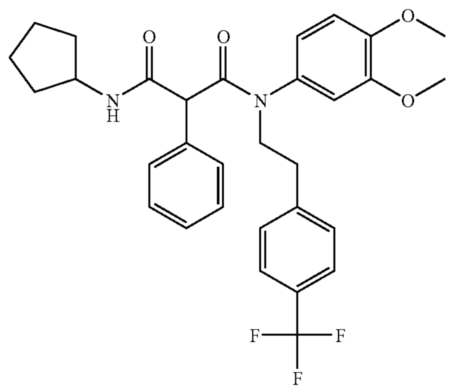 | 554.6 | N-Cyclopentyl-N'-(3,4-dimethoxy-phenyl)-2-phenyl-N'-[2-(4-trifluoromethyl-phenyl)-ethyl]-malonamide | N-(3,4-Dimethoxy-phenyl)-2-phenyl-N-[2-(4-trifluoromethyl-phenyl)-ethyl]-malonamic acid and cyclopentylamine (commercially available) | 555.4 |
| 5 | 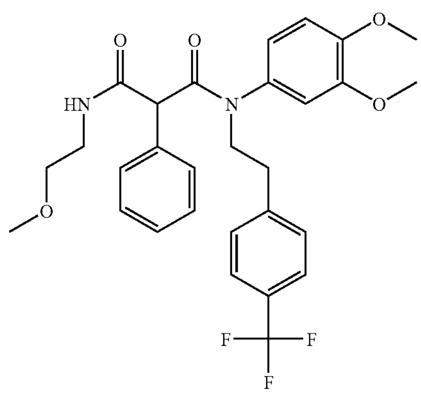 | 544.6 | N-(3,4-Dimethoxy-phenyl)-N'-[2-methoxy-ethyl]-2-phenyl-N-[2-(4-trifluoromethyl-phenyl)-ethyl]-malonamide | N-(3,4-Dimethoxy-phenyl)-2-phenyl-N-[2-(4-trifluoromethyl-phenyl)-ethyl]-malonamic acid and 2-Methoxy-ethylamine (commercially available) | 545.3 |
| 6 | 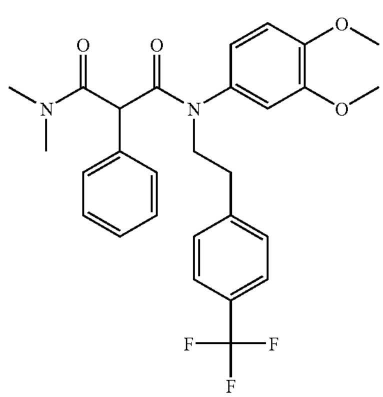 | 514.5 | N-(3,4-Dimethoxy-phenyl)-N',N'-dimethyl-2-phenyl-N-[2-(4-trifluoromethyl-phenyl)-ethyl]-malonamide | N-(3,4-Dimethoxy-phenyl)-2-phenyl-N-[2-(4-trifluoromethyl-phenyl)-ethyl]-malonamic acid and dimethylamine (commercially available) | 515.3 |
| 7 | 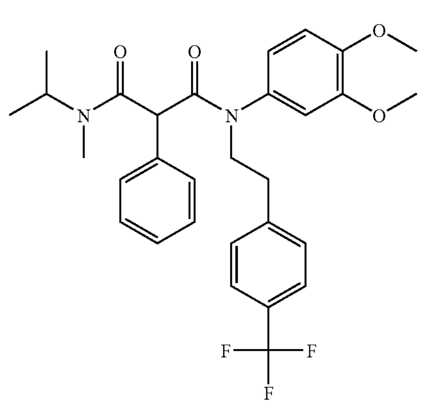 | 542.6 | N-(3,4-Dimethoxy-phenyl)-N'-isopropyl-N'-methyl-2-phenyl-N-[2-(4-trifluoromethyl-phenyl)-ethyl]-malonamide | N-(3,4-Dimethoxy-phenyl)-2-phenyl-N-[2-(4-trifluoromethyl-phenyl)-ethyl]-malonamic acid and Isopropyl-methyl-amine (commercially available) | 543.4 |

TABLE 1-continued

| No | structure | MW | name | starting material | MW MH+ found |
|----|-----------|------|------|-------------------|--------------|
| 8  | 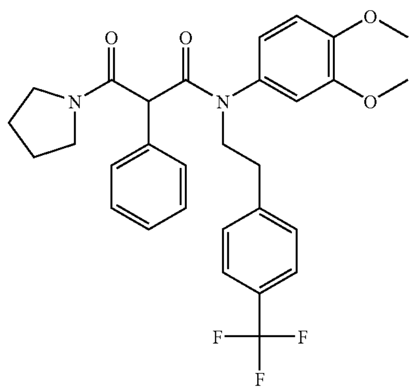          | 540.6 | N-(3,4-Dimethoxy-phenyl)-3-oxo-2-phenyl-3-pyrrolidin-1-yl-N-[2-(4-trifluoromethyl-phenyl)-ethyl]-propionamide | N-(3,4-Dimethoxy-phenyl)-2-phenyl-N-[2-(4-trifluoromethyl-phenyl)-ethyl]-malonamic acid and pyrrolidine (commercially available) | 541.3 |
| 9  | 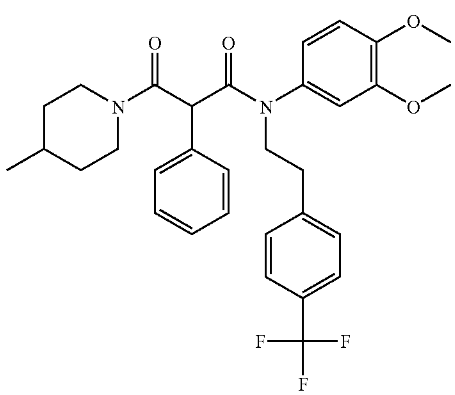          | 568.6 | N-(3,4-Dimethoxy-phenyl)-3-(4-methyl-piperdin-1-yl)-3-oxo-2-phenyl-N-[2-(4-trifluoromethyl-phenyl)-ethyl]-propionamide | N-(3,4-Dimethoxy-phenyl)-2-phenyl-N-[2-(4-trifluoromethyl-phenyl)-ethyl]-malonamic acid and 4-Methyl-piperidine (commercially available) | 569.4 |
| 10 | 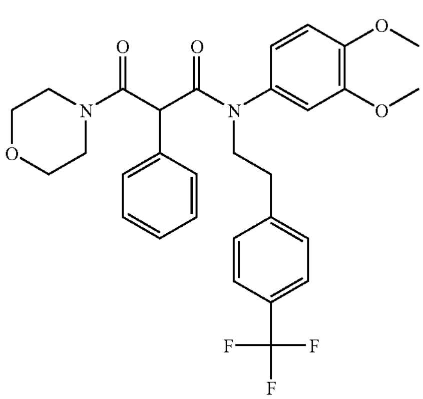          | 556.6 | N-(3,4-Dimethoxy-phenyl)-3-morpholin-4-yl-3-oxo-2-phenyl-N-[2-(4-trifluoromethyl-phenyl)-ethyl]-propionamide | N-(3,4-Dimethoxy-phenyl)-2-phenyl-N-[2-(4-trifluoromethyl-phenyl)-ethyl]-malonamic acid and morpholine (commerecially available) | 557.4 |

TABLE 1-continued

| No | structure | MW | name | starting material | MW MH+ found |
|---|---|---|---|---|---|
| 11 | 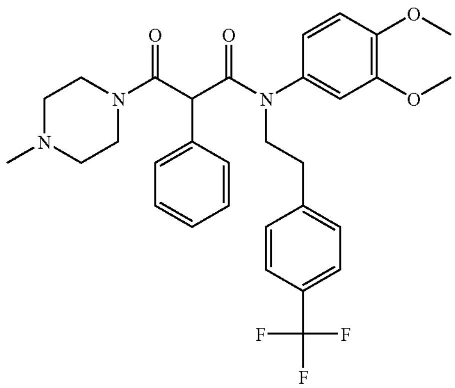 | 569.6 | N-(3,4-Dimethoxy-phenyl)-3-(4-methyl-piperazin-1-yl)-3-oxo-2-phenyl-N-[2-(4-trifluoromethyl-phenyl)-ethyl]-propionamide | N-(3,4-Dimethoxy-phenyl)-2-phenyl-N-[2-(4-trifluoromethyl-phenyl)-ethyl]-malonamic acid and 1-Methyl-piperazine (commercially available) | 570.4 |
| 12 | 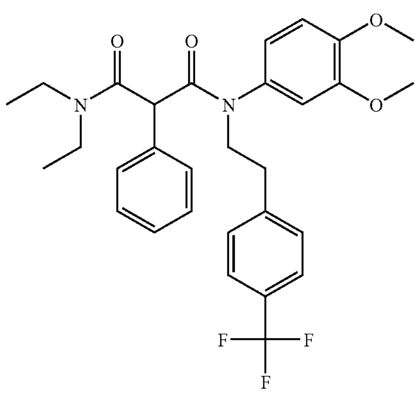 | 542.6 | N-(3,4-Dimethoxy-phenyl)-N',N'-diethyl-2-phenyl-N-[2-(4-trifluoromethyl-phenyl)-ethyl]-malonamide | N-(3,4-Dimethoxy-phenyl)-2-phenyl-N-[2-(4-trifluoromethyl-phenyl)-ethyl]-malonamic acid and diethylamine (commercially available) | 543.4 |
| 13 | 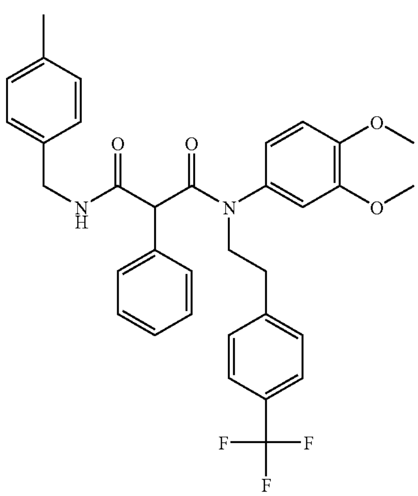 | 590.6 | N-(3,4-Dimethoxy-phenyl)-N'-(4-methyl-benzyl)-2-phenyl-N-[2-(4-trifluoromethyl-phenyl)-ethyl]-malonamide | N-(3,4-Dimethoxy-phenyl)-2-phenyl-N-[2-(4-trifluoromethyl-phenyl)-ethyl]-malonamic acid and 4-Methyl-benzylamine (commercially available) | 591.4 |

TABLE 1-continued

| No | structure | MW | name | starting material | MW MH+ found |
|---|---|---|---|---|---|
| 14 | 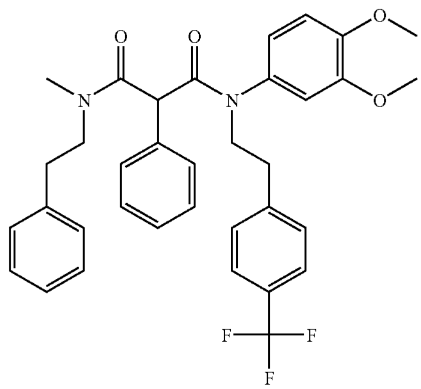 | 604.7 | N-(3,4-Dimethoxy-phenyl)-N'-methyl-N'-phenethyl-2-phenyl-N-[2-(4-trifluoromethyl-phenyl)-ethyl]-malonamide | N-(3,4-Dimethoxy-phenyl)-2-phenyl-N-[2-(4-trifluoromethyl-phenyl)-ethyl]-malonamic acid and Methyl-phenethyl-amine (commercially available) | 605.4 |
| 15 | 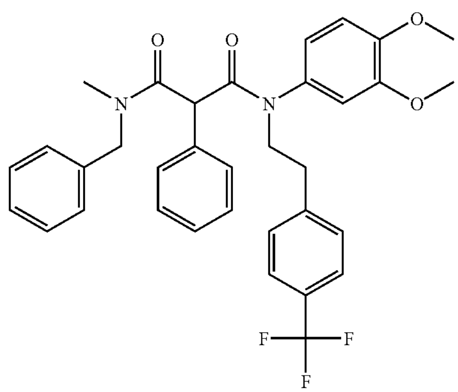 | 590.6 | N-Benzyl-N'-(3,4 dimethoxy-phenyl)-N-methyl-2-phenyl-N'-[2-(4-trifluoromethyl-phenyl)-ethyl]-malonamide | N-(3,4-Dimethoxy-phenyl)-2-phenyl-N-[2-(4-trifluoromethyl-phenyl)-ethyl]-malonamic acid and Benzyl-methyl-amine (commercially available) | 591.4 |
| 16 | 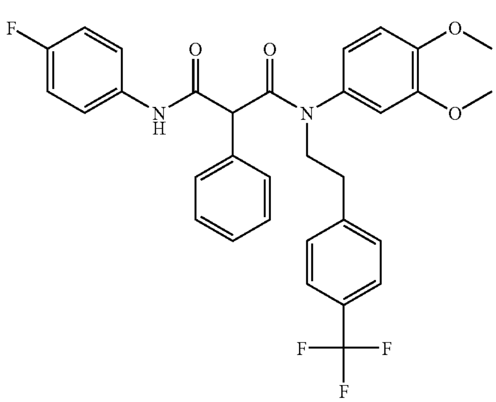 | 580.6 | N-(3,4-Dimethoxy-phenyl)-N'-(4-fluoro-phenyl)-2-phenyl-N-[2-(4-trifluoromethyl-phenyl)-ethyl]-malonamide | N-(3,4-Dimethoxy-phenyl)-2-phenyl-N-[2-(4-trifluoromethyl-phenyl)-ethyl]-malonamic acid and 4-Fluoro-phenylamine (commercially available) | 581.3 |

TABLE 1-continued

| No | structure | MW | name | starting material | MW MH+ found |
|---|---|---|---|---|---|
| 17 | 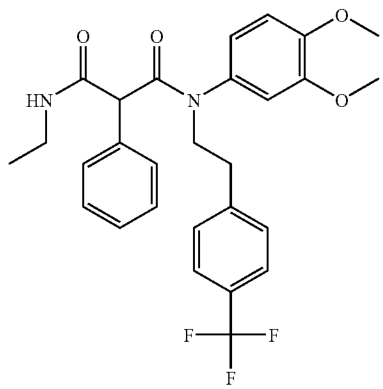 | 514.5 | N-(3,4-Dimethoxy-phenyl)-N'-ethyl-2-phenyl-N-[2-(4-trifluoromethyl-phenyl)-ethyl]-malonamide | N-(3,4-Dimethoxy-phenyl)-2-phenyl-N-[2-(4-trifluoromethyl-phenyl)-ethyl]-malonamic acid and ethylamine (commercially available) | 515.2 |
| 18 | 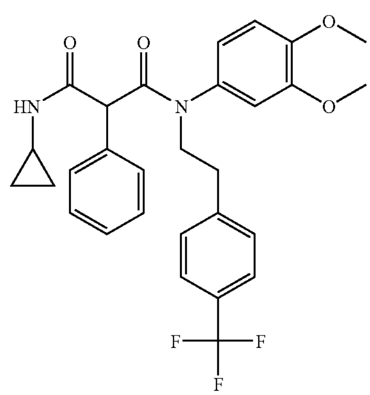 | 526.6 | N-Cyclopropyl-N'-(3,4-dimethoxy-phenyl)-2-phenyl-N'-[2-(4-trifluoromethyl-phenyl)-ethyl]-malonamide | N-(3,4-Dimethoxy-phenyl)-2-phenyl-N-[2-(4-trifluoromethyl-phenyl)-ethyl]-malonamic acid and cyclopropylamine (commercially available) | 527.2 |
| 19 | 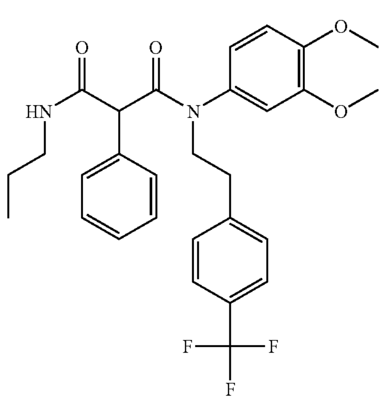 | 528.6 | N-(3,4-Dimethoxy-phenyl)-2-phenyl-N'-propyl-N-[2-(4-trifluoromethyl-phenyl)-ethyl]-malonamide | N-(3,4-Dimethoxy-phenyl)-2-phenyl-N-[2-(4-trifluoromethyl-phenyl)-ethyl]-malonamic acid and propylamine (commercially available) | 529.2 |

TABLE 1-continued

| No | structure | MW | name | starting material | MW MH+ found |
|---|---|---|---|---|---|
| 20 | 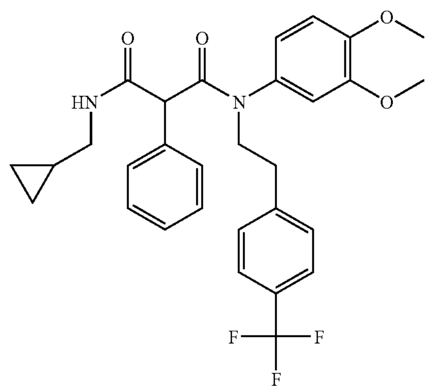 | 540.6 | N-Cyclopropylmethyl-N'-(3,4-dimethoxy-phenyl)-2-phenyl-N'-[2-(4-trifluoromethyl-phenyl)-ethyl]-malonamide | N-(3,4-Dimethoxy-phenyl)-2-phenyl-N-[2-(4-trifluoromethyl-phenyl)-ethyl]-malonamic acid and C-Cyclopropyl-methylamine (commercially available) | 541.2 |
| 21 | 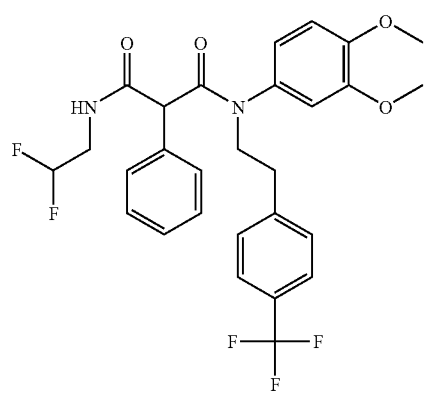 | 550.5 | N-(2,2-Difluoro-ethyl)-N'-(3,4-diemthoxy-phenyl)-2-phenyl-N'-[2-(4-trifluoromethyl-phenyl)-ethyl]-malonamide | N-(3,4-Diemthoxy-phenyl)-2-phenyl-N-[2-(4-trifluoromethyl-phenyl)-ethyl]-malonamic acid and 2,2-Difluoro-ethylamine (commercially available) | 551.2 |
| 22 | 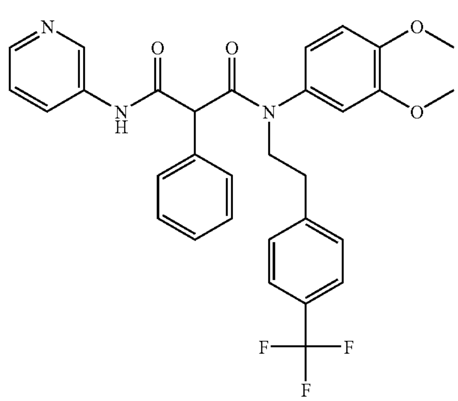 | 563.6 | N-(3,4-Dimethoxy-phenyl)-2-phenyl-N'-pyridin-3-yl-N-[2-(4-trifluoromethyl-phenyl)-ethyl]-malonamide | N-(3,4-Dimethoxy-phenyl)-2-phenyl-N-[2-(4-trifluoromethyl-phenyl)-ethyl]-malonamic acid and Pyridin-3-ylamine (commercially available) | 564.2 |

TABLE 1-continued

| No | structure | MW | name | starting material | MW MH+ found |
|---|---|---|---|---|---|
| 23 | 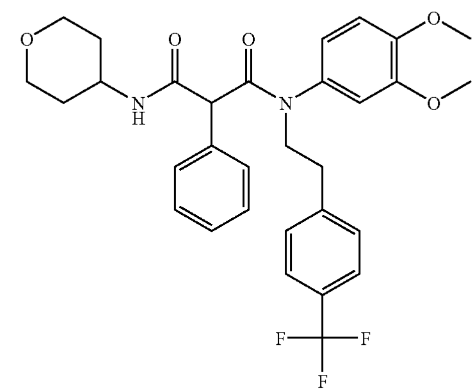 | 570.6 | N-(3,4-Dimethoxy-phenyl)-2-phenyl-N'-(tetrahydro-pyran-4-yl)-N-[2-(4-trifluoromethyl-phenyl)-ethyl]-malonamide | N-(3,4-Dimethoxy-phenyl)-2-phenyl-N-[2-(4-trifluoromethyl-phenyl)-ethyl]-malonamic acid and Tetrahydro-pyran-4-ylamine (commercially available) | 571.2 |
| 24 | 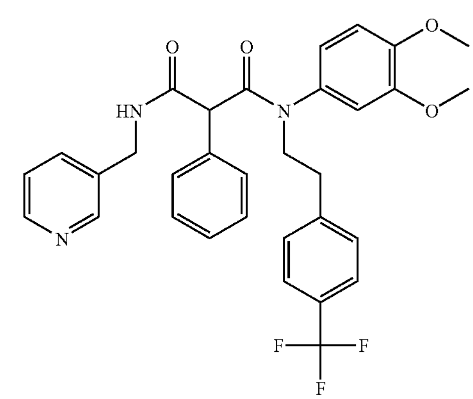 | 577.6 | N-(3,4-Dimethoxy-phenyl)-2-phenyl-N'-pyridin-3-ylmethyl-N-[2-(4-trifluoromethyl-phenyl)-ethyl]-malonamide | N-(3,4-Dimethoxy-phenyl)-2-phenyl-N-[2-(4-trifluoromethyl-phenyl)-ethyl]-malonamic acid and C-Pyridin-3-yl-methylamine (commercially available) | 578.2 |
| 25 | 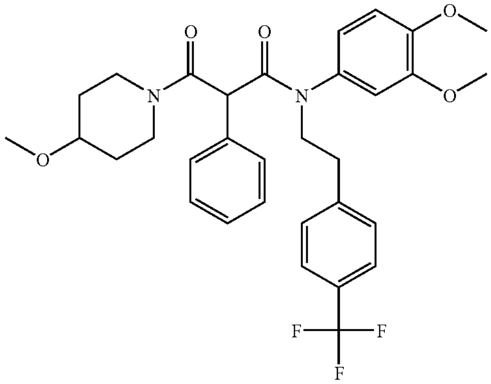 | 584.6 | N-(3,4-Dimethoxy-phenyl)-3-(4-methoxy-piperdin-1-yl)-3-oxo-2-phenyl-N-[2-(4-trifluoromethyl-phenyl)-ethyl]-propionamide | N-(3,4-Dimethoxy-phenyl)-2-phenyl-N-[2-(4-trifluoromethyl-phenyl)-ethyl]-malonamic acid and 4-Methoxy-piperidine (commercially available) | 585.3 |

TABLE 1-continued

| No | structure | MW | name | starting material | MW MH+ found |
|---|---|---|---|---|---|
| 26 | 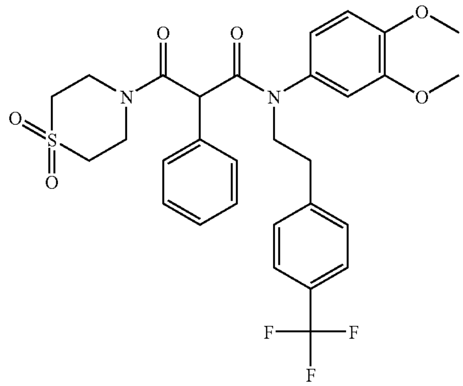 | 604.6 | N-(3,4-Dimethoxy-phenyl)-3-(1,1-dioxo-1λ⁶-thiomorpholin-4-yl)-3-oxo-2-phenyl-N-[2-(4-trifluoromethyl-phenyl)-ethyl]-propionamide | N-(3,4-Dimethoxy-phenyl)-2-phenyl-N-[2-(4-trifluoromethyl-phenyl)-ethyl]-malonamic acid and Thiomorpholine 1,1-dioxide (commercially available) | 605.2 |
| 27 | 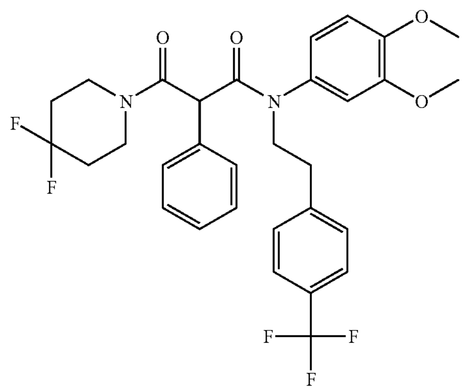 | 590.6 | 3-(4,4-Difluoro-piperdin-1-yl)-N-(3,4-dimethoxy-phenyl)-3-oxo-2-phenyl-N-[2-(4-trifluoromethyl-phenyl)-ethyl]-propionamide | N-(3,4-Dimethoxy-phenyl)-2-phenyl-N-[2-(4-trifluoromethyl-phenyl)-ethyl]-malonamic acid and 4,4-Difluoro-piperdine (commercially available) | 591.2 |

In analogy to the procedure described for the synthesis of (3,4-Dimethoxy-phenyl)-[2-(4-trifluoromethyl-phenyl)-ethyl]-amine (intermediate 1) further phenethylamines have been synthesized from the starting materials mentioned in table 2 through amide coupling and subsequent reduction. Table 2 comprises intermediate 2-intermediate 24.

TABLE 2

| Intermediate | structure | MW | name | starting materials | MW found |
|---|---|---|---|---|---|
| 2 | 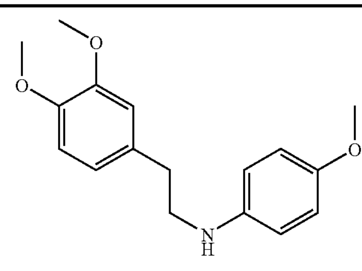 | 287.4 | [2-(3,4-Dimethoxy-phenyl)-ethyl]-(4-methoxy-phenyl)-amine | (3,4-Dimethoxy-phenyl)-acetic acid and 4-Methoxy-phenylamine | 288.1 |
| 3 | 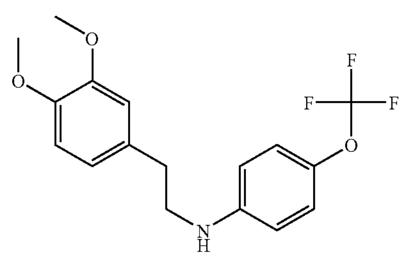 | 341.3 | [2-(3,4-Dimethoxy-phenyl)-ethyl]-(4-trifluoromethoxy-phenyl)-amine | (3,4-Dimethoxy-phenyl)-acetic acid and 4-Trifluoromethoxy-phenylamine | 342.1 |

TABLE 2-continued

| Intermediate | structure | MW | name | starting materials | MW found |
|---|---|---|---|---|---|
| 4 | 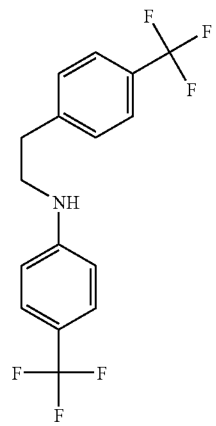 | 333.3 | (4-Trifluoromethyl-phenyl)-[2-(4-trifluoromethyl-phenyl)-ethyl]-amine | (4-Trifluoromethyl-phenyl)-acetic acid and 4-Trifluoromethyl-phenylamine | 334 |
| 5 | 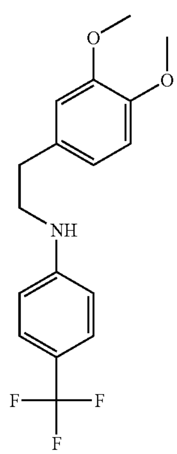 | 325.3 | [2-(3,4-Dimethoxy-phenyl)-ethyl]-(4-trifluoromethyl-phenyl)-amine | (3,4-Dimethoxy-phenyl)-acetic acid and 4-Trifluoromethyl-phenylamine | 326 |
| 6 | 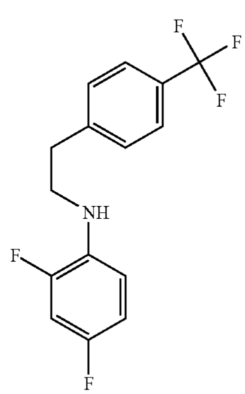 | 301.3 | (2,4-Difluoro-phenyl)-[2-(4-trifluoromethyl-phenyl)-ethyl]-amine | (4-Trifluoromethyl-phenyl)-acetic acid and 2,4-Difluoro-phenylamine | 302 |

TABLE 2-continued

| Intermediate | structure | MW | name | starting materials | MW found |
|---|---|---|---|---|---|
| 7 | 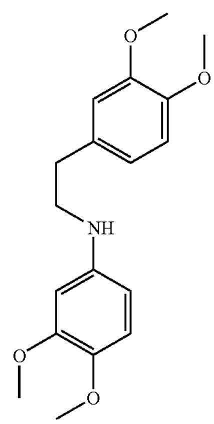 | 317.4 | (3,4-Dimethoxy-phenyl)-[2-(3,4-dimethoxy-phenyl)-ethyl]-amine | (3,4-Dimethoxy-phenyl)-acetic acid and 3,4-Dimethoxy-phenylamine | 318 |
| 8 | 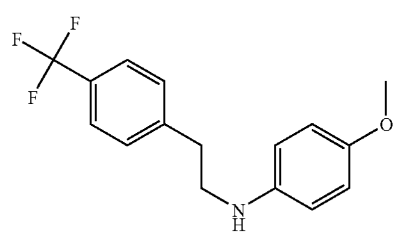 | 295.3 | (4-Methoxy-phenyl)-[2-(4-trifluoromethyl-phenyl)-ethyl]-amine | (4-Trifluoromethyl-phenyl)-acetic acid and 4-Methoxy-phenylamine | 296 |
| 9 | 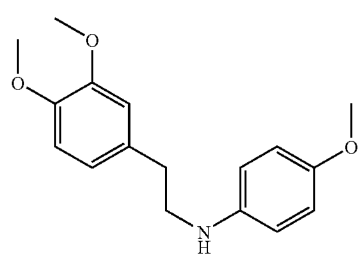 | 287.4 | [2-(3,4-Dimethoxy-phenyl)-ethyl]-(4-methoxy-phenyl)-amine | (3,4-Dimethoxy-phenyl)-acetic acid and 4-Methoxy-phenylamine | 288.1 |
| 10 | 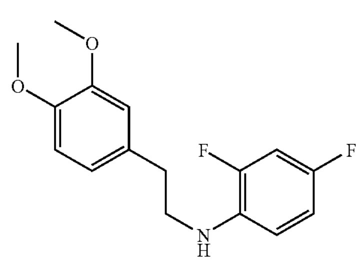 | 293.3 | (2,4-Difluoro-phenyl)-[2-(3,4-dimethoxy-phenyl)-ethyl]-amine | (3,4-Diemthoxy-phenyl)-acetic acid and 2,4-Difluoro-phenylamine | 294 |

TABLE 2-continued

| Intermediate | structure | MW | name | starting materials | MW found |
|---|---|---|---|---|---|
| 11 | 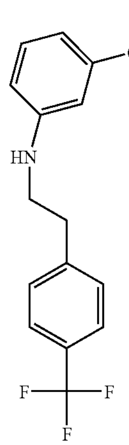 | 295.3 | (3-Methoxy-phenyl)-[2-(4-trifluoromethyl-phenyl)-ethyl]-amine | (4-Trifluoromethyl-phenyl)-acetic acid and 3-Methoxy-phenylamine | 296 |
| 12 | 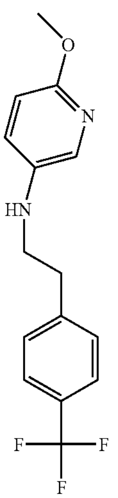 | 296.3 | (6-Methoxy-pyridin-3-yl)-[2-(4-trifluoromethyl-phenyl)-ethyl]-amine | (4,-Trifluoromethyl-phenyl)-acetic acid and 6-Methoxy-pyridin-3-ylamine | 297 |
| 13 | 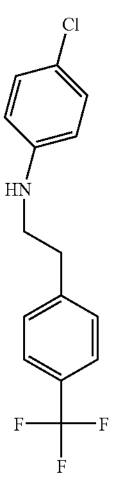 | 299.7 | (4-Chloro-phenyl)-[2-(4-trifluoromethyl-phenyl)-ethyl]-amine | (4-Trifluoromethyl-phenyl)-acetic acid and 4-Chloro-phenylamine | 300 |

TABLE 2-continued

| Intermediate | structure | MW | name | starting materials | MW found |
|---|---|---|---|---|---|
| 14 | 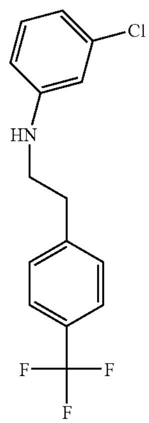 | 299.7 | (3-Chloro-phenyl)-[2-(4-trifluoromethyl-phenyl)-ethyl]-amine | (4-Trifluoromethyl-phenyl)-acetic acid and 3-Chloro-phenylamine | 300 |
| 15 | 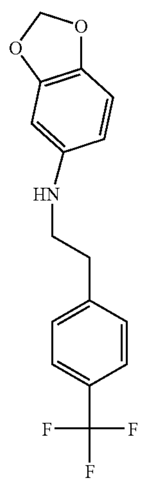 | 309.3 | Benzo[1,3]dioxol-5-yl-[2-(4-trifluoromethyl-phenyl)-ethyl]-amine | (4-Trifluoromethyl-phenyl)-acetic acid and Benzo[1,3]dioxol-5-ylamine | 310 |
| 16 | 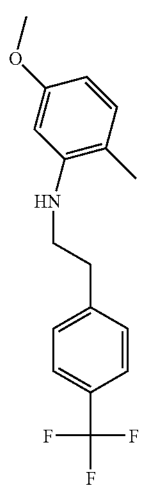 | 309.3 | (5-Methoxy-2-methyl-phenyl)-[2-(4-trifluoromethyl-phenyl)-ethyl]-amine | (4-Trifluoromethyl-phenyl)-acetic acid and 5-Methoxy-2-methyl-phenylamine | 310 |

TABLE 2-continued

| Intermediate | structure | MW | name | starting materials | MW found |
|---|---|---|---|---|---|
| 17 | 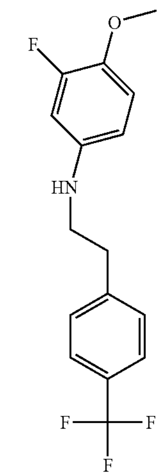 | 313.3 | (3-Fluoro-4-methoxy-phenyl)-[2-(4-trifluoromethyl-phenyl)-ethyl]-amine | (4-Trifluoromethyl-phenyl)-acetic acid and 3-Fluoro-4-methoxy-phenylamine | 314 |
| 18 | 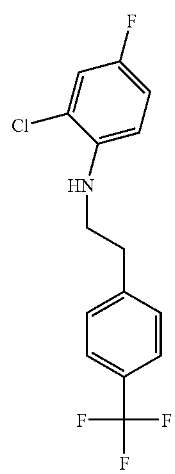 | 317.7 | (2-Chloro-4-fluoro-phenyl)-[2-(4-trifluoromethyl-phenyl)-ethyl]-amine | (4-Trifluoromethyl-phenyl)-acetic acid and 2-Chloro-4-fluoro-phenylamine | 318 |
| 19 | 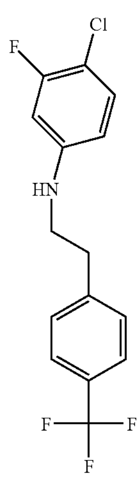 | 317.7 | (4-Chloro-3-fluoro-phenyl)-[2-(4-trifluoromethyl-phenyl)-ethyl]-amine | (4-Trifluoromethyl-phenyl)-acetic acid and 4-Chloro-3-fluoro-phenylamine | 317.9 |

TABLE 2-continued

| Intermediate | structure | MW | name | starting materials | MW found |
|---|---|---|---|---|---|
| 20 | 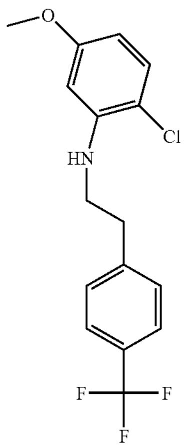 | 329.7 | (2-Chloro-5-methoxy-phenyl)-[2-(4-trifluoromethyl-phenyl)-ethyl]-amine | (4-Trifluoromethyl-phenyl)-acetic acid and 2-Chloro-5-methoxy-phenylamine | 330 |
| 21 | 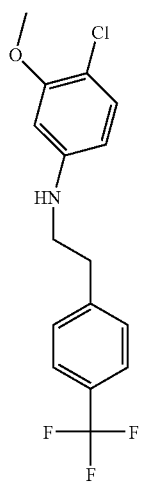 | 329.7 | (4-Chloro-3-methoxy-phenyl)-[2-(4-trifluoromethyl-phenyl)-ethyl]-amine | (4-Trifluoromethyl-phenyl)-acetic acid and 4-Chloro-3-methoxy-phenylamine | 330 |
| 22 | 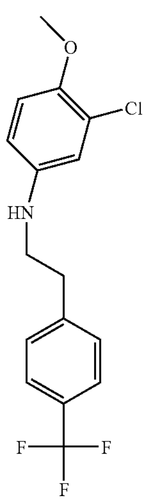 | 329.7 | (3-Chloro-4-methoxy-phenyl)-[2-(4-trifluoromethyl-phenyl)-ethyl]-amine | (4-Trifluoromethyl-phenyl)-acetic acid and 3-Chloro-4-methoxy-phenylamine | 330 |

TABLE 2-continued

| Intermediate | structure | MW | name | starting materials | MW found |
|---|---|---|---|---|---|
| 23 | 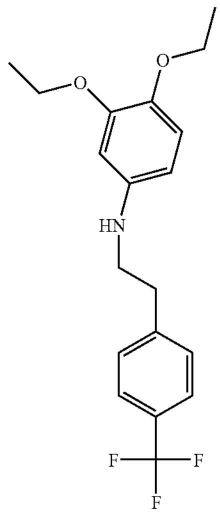 | 353.4 | (3,4-Diethoxy-phenyl)-[2-(4-trifluoromethyl-phenyl)-ethyl]-amine | (4-Trifluoromethyl-phenyl)-acetic acid and 3,4-Diethoxy-phenylamine | 354.2 |
| 24 | 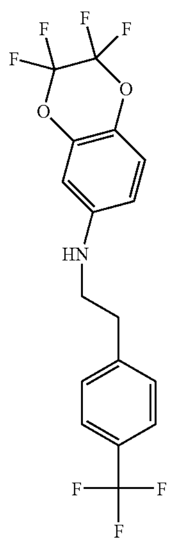 | 395.3 | (2,2,3,3-Tetrafluoro-2,3-dihydro-benzo[1,4]dioxin-6-yl)-[2-(4-trifluoromethyl-phenyl)-ethyl]-amine | (4-Trifluoromethyl-phenyl)-acetic acid and 2,2,3,3-Tetrafluoro-2,3-dihydro-benzo[1,4]dioxin-6-ylamine | 395.1 |

EXAMPLE 28

N-[2-(3,4-Dimethoxy-phenyl)-ethyl]-N-(4-methoxy-phenyl)-N',N'-dimethyl-2-phenyl-malonamide

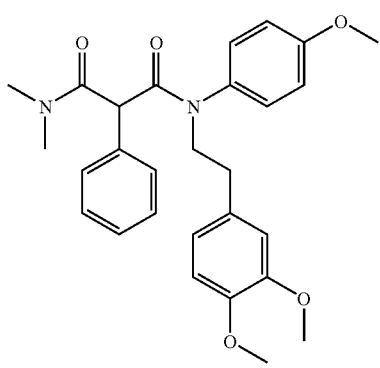

A mixture of 28.7 mg (0.1 mmol) [2-(3,4-Dimethoxy-phenyl)-ethyl]-(4-methoxy-phenyl)-amine (intermediate 2), 20.7 mg (0.1 mmol) N,N-Dimethyl-2-phenyl-malonamic acid (WO2000009481), 38.5 mg (0.12 mmol) TBTU and 38.7 mg (0.3 mmol) DIPEA in 3 mL DMF was stirred at room temperature for 16 h. The mixture was concentrated diluted with methanol and formic acid and purified by preparative HPLC on reversed phase eluting with a gradient formed from acetonitrile, water and formic acid, the product containing fractions were evaporated to yield 23.2 mg (61%) of the title compound. MS(m/e): 477.2 (MH+).

In analogy to the procedure described for the synthesis of example 28 further malonamide derivatives have been synthesized from their respective starting materials mentioned in table 3. The examples are shown in table 3 and comprise example 29-example 62.

TABLE 3

| No | structure | MW | name | starting material | MW MH+ found |
|----|-----------|-----|------|-------------------|--------------|
| 28 | 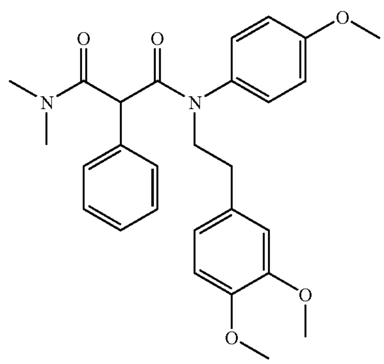 | 476.6 | N-[2-(3,4-Dimethoxy-phenyl)-ethyl]-N-(4-methoxy-phenyl)-N',N'-dimethyl-2-phenyl-malonamide | N,N-Dimethyl-2-phenyl-malonamic acid (WO000009481) and [2-(3,4-Dimethoxy-phenyl)-ethyl]-(4-methoxy-phenyl)-amine (intermediate 2) | 477.2 |
| 29 | 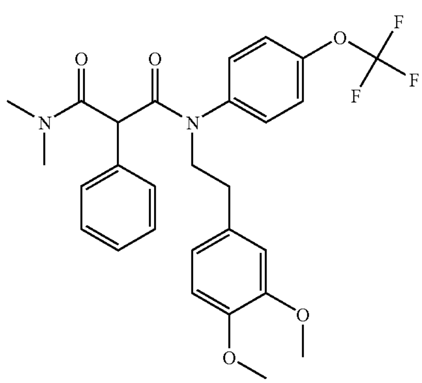 | 530.5 | N-[2-(3,4-Dimethoxy-phenyl)-ethyl]-N',N'-dimethyl-2-phenyl-N-(4-trifluoromethoxy-phenyl)-malonamide | N,N-Dimethyl-2-phenyl-malonamic acid (WO000009481) and [2-(3,4-Dimethoxy-phenyl)-ethyl]-(4-trifluoromethoxy-phenyl)-amine (Intermediate 3) | 531.2 |
| 30 | 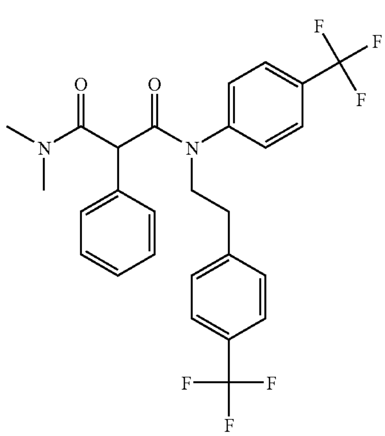 | 522.5 | N,N-Dimethyl-2 phenyl-N'-(4-trifluoromethyl-phenyl)-N'-[2-(4-trifluoromethyl-phenyl)-ethyl]-malonamide | N,N-Dimethyl-2-phenyl-malonamic acid (WO000009481) and (4-Trifluoromethyl-phenyl)-[2-(4-trifluoromethyl-phenyl)-ethyl]-amine (intermediate 4) | 523.2 |

TABLE 3-continued

| No | structure | MW | name | starting material | MW MH+ found |
|---|---|---|---|---|---|
| 31 | 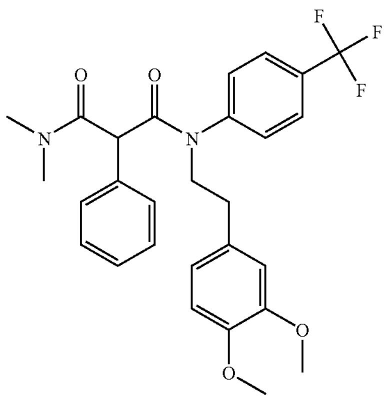 | 514.5 | N-[2-(3,4-Dimethoxy-phenyl)-ethyl]-N',N'-dimethyl-2-phenyl-N-(4-trifluoromethyl-phenyl)-malonamide | N,N-Dimethyl-2-phenyl-malonamic acid (WO000009481) and [2-(3,4-Dimethoxy-phenyl)-ethyl]-(4-trifluoromethyl-phenyl)-amine (intermediate 5) | 515.2 |
| 32 | 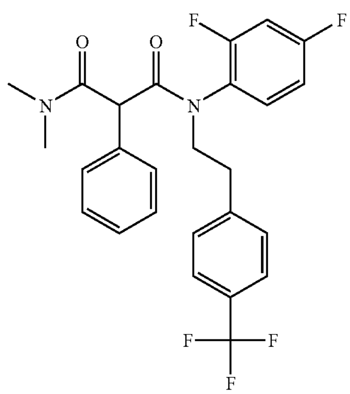 | 490.5 | N-(2,4-Difluoro-phenyl)-N',N'-dimethyl-2-phenyl N-[2-(4-trifluoromethyl-phenyl)ethyl]-malonamide | N,N-Dimethyl-2-phenyl-malonmaic acid (WO000009481) and (2,4-Difluoro-phenyl)-[2-(4-trifluoromethyl-phenyl)-ethyl]-amine (intermediate 6) | 491.1 |
| 33 | 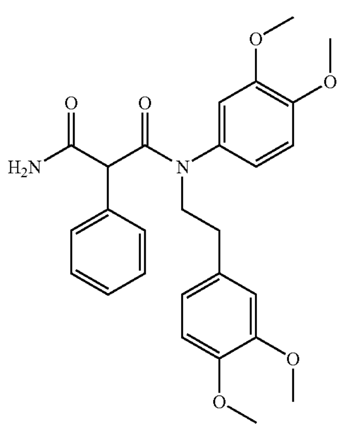 | 478.5 | N-(3,4-Dimethoxy-phenyl)-N-[2-(3,4-dimethoxy-phenyl)-ethyl]-2-phenyl-malonamide | 2-Phenyl-malonamic acid (JACS 1955, 77, 4849-51) and (3,4-Dimethoxy-phenyl)-[2-(3,4-dimethoxy-phenyl)-ethyl]-amine (intermediate 7) | 479.2 |

TABLE 3-continued

| No | structure | MW | name | starting material | MW MH+ found |
|---|---|---|---|---|---|
| 34 | 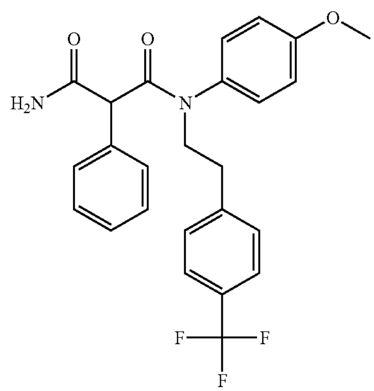 | 456.5 | N-(4-Methoxy-phenyl)-2-phenyl-N-[2-(4-trifluoromethyl-phenyl)-ethyl]-malonamide | 2-Phenyl-malonamic acid (JACS 1955, 77, 4849-51) and (4-Methoxy-phenyl)-[2-(4-trifluoromethyl-phenyl)-ethyl]-amine (intermediate 8) | 457.1 |
| 35 | 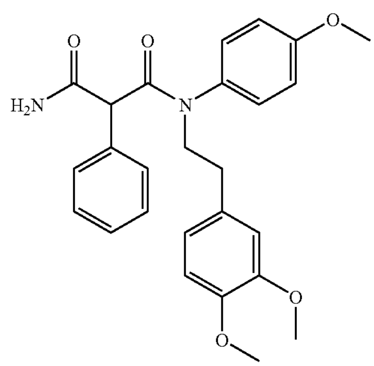 | 448.5 | N-[2-(3,4-Dimethoxy-phenyl)-ethyl]-N-(4-methoxy-phenyl)-2-phenyl-malonamide | 2-Phenyl-malonamic acid (JACS 1955, 77, 7849-51) and [2-(3,4-Dimethoxy phenyl)-ethyl]-(4-methoxy-phenyl)-amine (intermediate 9) | 449.1 |
| 36 | 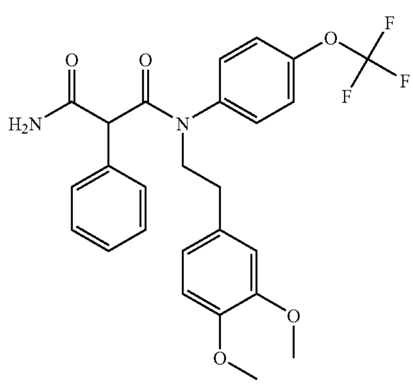 | 502.5 | N-[2-(3,4-Dimethoxy-phenyl)-ethyl]-2-phenyl-N-(4-trifluoromethoxy-phenyl)-malonamide | 2-Phenyl-malonamic acid (JACS 1955, 77, 4849-51) and [2-(3,4-Dimethoxy-phenyl)-ethyl]-(4-trifluoromethoxy-phenyl)-amine (intermediate 3) | 503.1 |
| 37 | 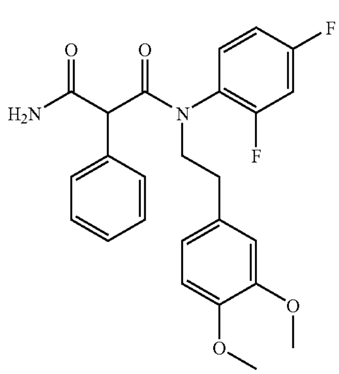 | 454.5 | N-(2,4-Difluoro-phenyl)-N-[2-(3,4-dimethoxy-phenyl)-ethyl]-2-phenyl-malonamide | 2-Phenyl-malonamic acid (JACS 1955, 77, 4849-51) and (2,4,-Difluoro-phenyl)-[2-(3,4-dimethoxy-phenyl)-ethyl]-amine (intermediate 10) | 455.1 |

TABLE 3-continued

| No | structure | MW | name | starting material | MW MH+ found |
|---|---|---|---|---|---|
| 38 | 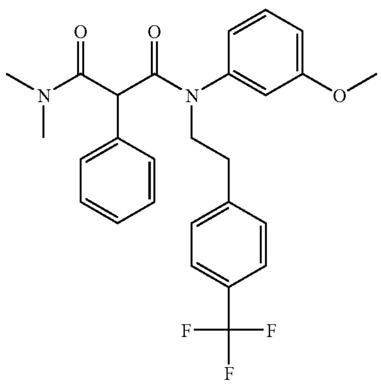 | 484.5 | N-(3-Methoxy-phenyl)-N',N'-dimethyl-2-phenyl-N-[2-(4-trifluoromethyl phenyl)-ethyl]-malonamide | N,N-Dimethyl-2-phenyl-malonamic acid (WO000009481) and (3-Methoxy-phenyl)-[2-(4-trifluoromethyl-phenyl)-ethyl]-amine (intermidiate 11) | 485.2 |
| 39 | 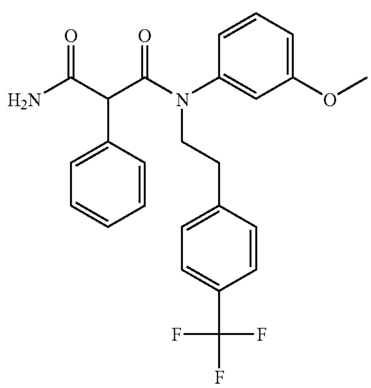 | 456.5 | N-(3-Methoxy-phenyl)-2-phenyl-N-[2-(4-trifluoromethyl-phenyl)-ethyl]-malonamide | 2-Phenyl-malonamic acid (JACS 1955, 77, 4849-51) and (3-Methoxy-phenyl)-[2-(4-trifluoromethyl-phenyl)-ethyl]-amine (intermediate 11) | 457.1 |
| 40 | 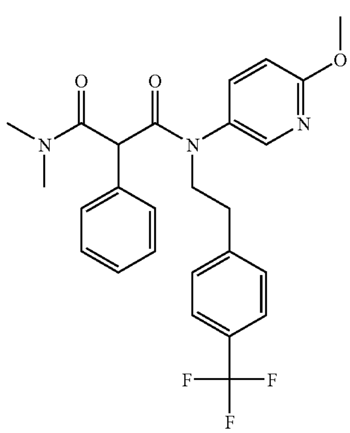 | 485.5 | N-(6-Methoxy-pyridin-3-yl)-N',N'-dimethyl-2-phenyl-N-[2-(4-trifluoromethyl-phenyl)-ethyl]-malonamide | N,N-Dimethyl-2-phenyl-malonamic acid (WO000009481) and (6-Methoxy-pyridin-3-yl)-[2-(4-trifluoromethyl-phenyl)-ethyl]-amine (intermediate 12) | 486.2 |

TABLE 3-continued

| No | structure | MW | name | starting material | MW MH+ found |
|---|---|---|---|---|---|
| 41 | 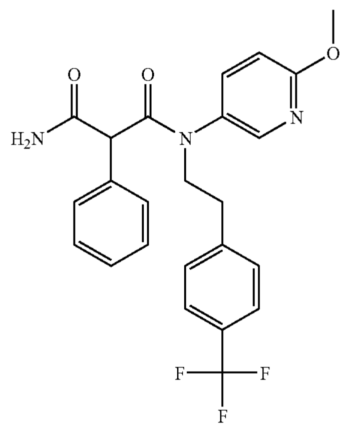 | 457.5 | N-(6-Methoxy-pyridin-3-yl)-2-phenyl-N-[2-(4-trifluoromethyl-phenyl)-ethyl]-malonaide | 2-Phenyl-malonamic acid (JACS 1955, 77, 4849-51) and (6-Methoxy-pyridin-3-yl)-[2-(4-trifluoromethyl-phenyl)-ethyl]-amine (intermediate 12) | 458.2 |
| 42 | 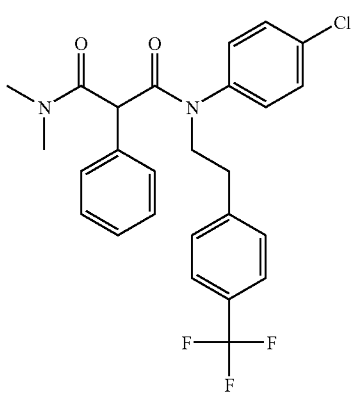 | 488.9 | N-(4-Chloro-phenyl)-N',N'-dimethyl-2-phenyl-N-[2-(4-trifluoromethyl-phenyl)-ethyl]-malonamide | N,N-Dimethyl-2-phenyl-malonamic acid (WO000009481) and (4-Chloro-phenyl)-[2-(4-trifluoromethyl-phenyl)-ethyl]-amine (intermediate 13) | 489.1 |
| 43 | 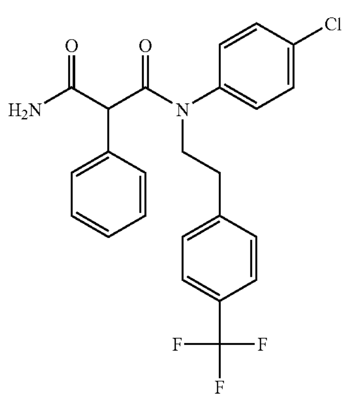 | 460.9 | N-(4-Chloro-phenyl)-2-phenyl-N-[2-(4-trifluoromethyl-phenyl)-ethyl]-malonamide | 2-Phenyl-malonamic acid (JACS 1955, 77, 4849-51) and (4-Chloro-phenyl)-[2-(4-trifluoromethyl-phenyl)-ethyl]-amine (intermediate 13) | 461.1 |

TABLE 3-continued

| No | structure | MW | name | starting material | MW MH+ found |
|---|---|---|---|---|---|
| 44 | 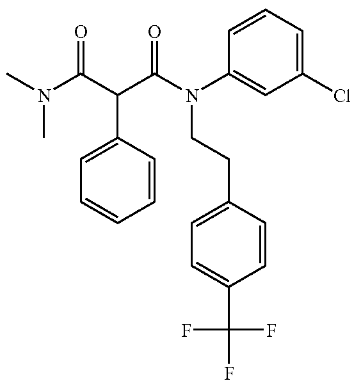 | 488.9 | N-(3-Chloro-phenyl)-N',N'-dimethyl-2-phenyl-N-[2-(4-trifluoromethyl-phenyl)-ethyl]-malonamide | N,N-Dimethyl-2-phenyl malonamic acid (WO000009481 and (3-Chloro-phenyl)-[2-(4-trifluoromethyl-phenyl)-ethyl]-amine intermdediate 14) | 498.1 |
| 45 | 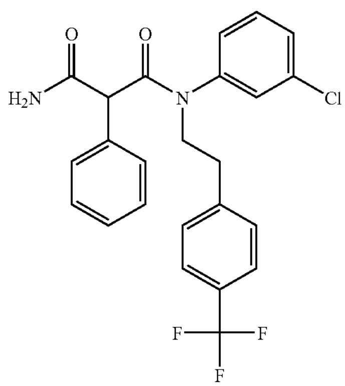 | 460.9 | N-(3-Chloro-phenyl)-2-phenyl-N-[2-(4-trifluoromethyl-phenyl)-ethyl]-malonamide | 2-Phenyl-malonamic acid (JACS 1955, 77, 4849-51) and (3-Chloro-phenyl)-[2-(4-trifluoromethyl-phenyl)-ethyl]-amine (intermediate 14) | 461.1 |
| 46 | 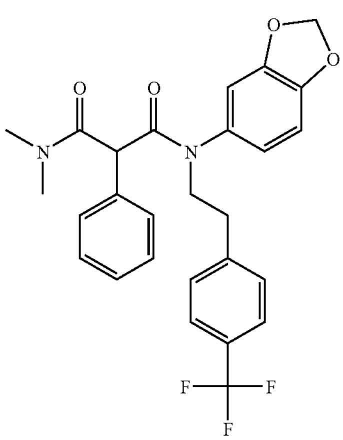 | 498.5 | N-Benzo[1,3]dioxol-5-yl-N',N'-dimethyl-2-phenyl-N-[2-(4-trifluoromethyl-phenyl)-ethyl]-malonamide | N,N-Dimethyl-2-phenyl-malonamic acid (WO000009481) and Benzo[1,3]dioxol-5-yl-[2-(4-trifluoromethyl-phenyl)-ethyl]-amine (intermediate 15) | 501.2 |

TABLE 3-continued

| No | structure | MW | name | starting material | MW MH+ found |
|---|---|---|---|---|---|
| 47 | 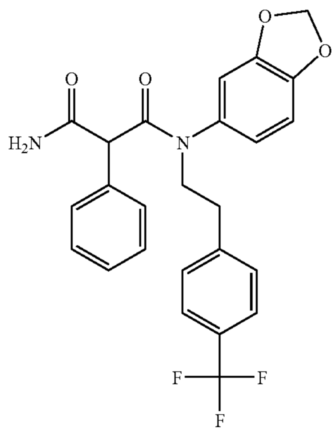 | 470.4 | N-Benzo[1,3]dioxol-5-yl-2-phenyl-N-[2-(4-trifluoromethyl-phenyl)-ethyl]-malonamide | 2-Phenyl-malonamic acid (JACS 1955, 77, 4849-51) and Benzo[1,3]dioxol-5-yl-[2-(4-trifluoromethyl-phenyl)-ethyl]amine (intermediate 15) | 471.1 |
| 48 | 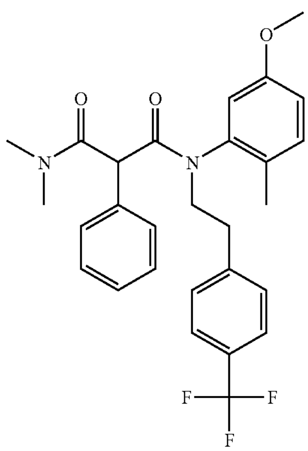 | 498.5 | N-(5-Methoxy-2-methyl-phenyl)-N',N'-dimethyl-2-phenyl-N-[2-(4-trifluoromethyl-phenyl)-ethyl]-malonamide | N,N-Dimethyl-2-phenyl-malonamic acid (WO000009481) and (5-Methoxy-2-methyl-phenyl)-[2-(4-trifluoromethyl-phenyl)ethyl]-amine(3-Methoxy-phenyl)-[2-(4-trifluoromethyl-phenyl)-ethyl]-amine (intermediate 16) | 499.2 |
| 49 | 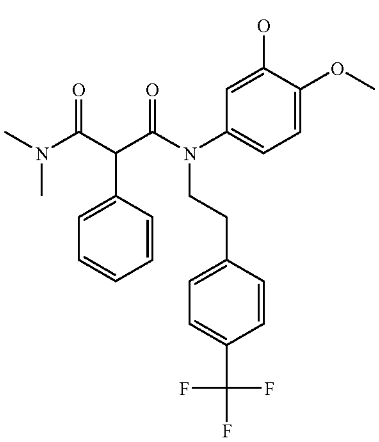 | 502.5 | N-(3-Fluoro-4-methoxy-phenyl)-N',N'-dimethyl-2-phenyl-N-[2-(4-trifluoromethyl-phenyl)-ethyl]-malonamide | N,N-Dimethyl-2-phenyl-malonamic acid (WO000009481) and (3-Fluoro-4-methoxy-phenyl)-[2-(4-trifluoromethyl-phenyl)-ethyl]-amine (intermediate 17) | 503.2 |

TABLE 3-continued

| No | structure | MW | name | starting material | MW MH+ found |
|---|---|---|---|---|---|
| 50 | 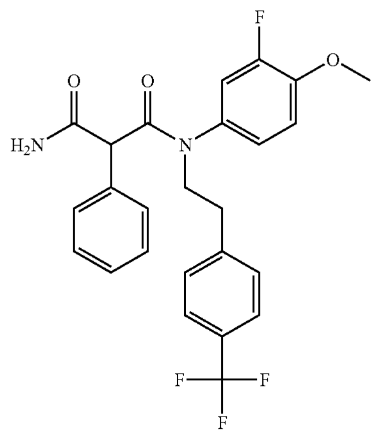 | 474.5 | N-(3-Fluoro-4-methoxy-phenyl)-2-phenyl-N-[2-(4-trifluoromethyl-phenyl)-ethyl]-malonamide | 2-Phenyl-malonamic acid (JACS 1955, 77, 4849-51) and (3-Fluoro-4-methoxy-phenyl)-[2-(4-trifluoromethyl-phenyl)-ethyl]-amine (intermediate 17) | 475.2 |
| 51 | 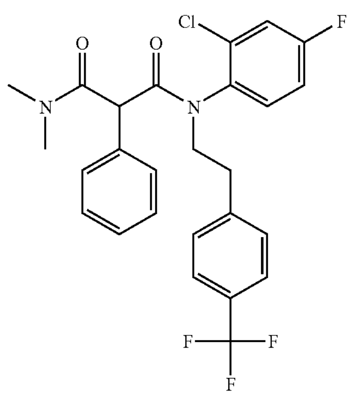 | 506.9 | N-(2-Chloro-4-fluoro-phenyl)-N',N'-dimethyl-2-phenyl-N-[2-(4-trifluoromethyl-phenyl)-ethyl]-malonamide | N,N-Dimethyl-3-phenyl-malonamic acid (WO000009481) and (2-Chloro-4-fluoro-phenyl)-[2-(4-trifluoromethyl-phenyl)-ethyl]-amine (intermediate 18) | 507.2 |
| 52 | 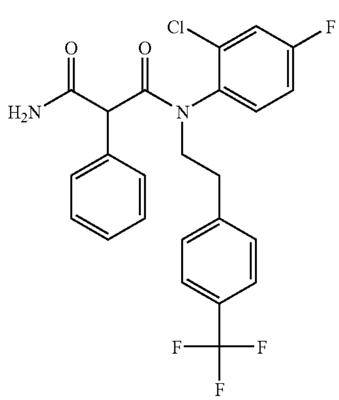 | 478.9 | N-(2-Chloro-4-fluoro-phenyl)-2-phenyl-N-[2-(4-trifluoromethyl-phenyl)-ethyl]-malonamide | 2-Phenyl-malonamic acid (JACS 1955, 77, 4849-51) and (2-Chloro-4-fluoro-phenyl)-[2-(4-trifluoromethyl-phenyl)-ethyl]-amine (intermediate 18) | 479.1 |

TABLE 3-continued

| No | structure | MW | name | starting material | MW MH+ found |
|---|---|---|---|---|---|
| 53 | 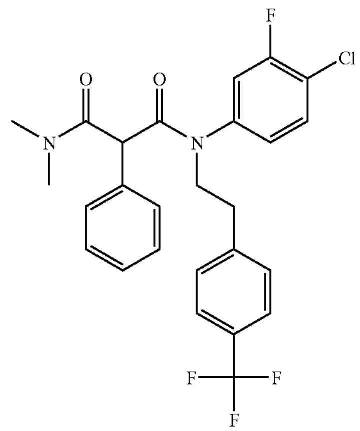 | 506.9 | N-(4-Chloro-3-fluoro-phenyl)-N',N'-dimethyl-2-phenyl-N-[2-(4-trifluoromethyl-phenyl)-ethyl]-malonamide | N,N-Dimethyl-2-phenyl-malonamic acid (WO000009481) and (4-Chloro-3-fluoro-phenyl)-[2-(4-trifluoromethyl-phenyl)-ethyl]-amine (intermediate 19) | 507.1 |
| 54 | 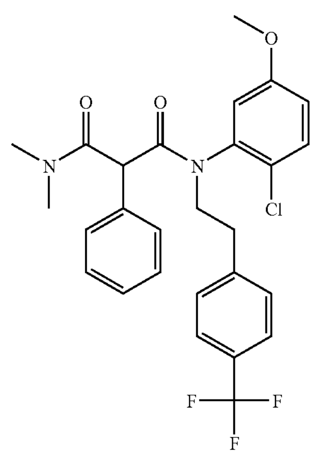 | 519.0 | N-(2-Chloro-5-methoxy-phenyl)-N',N'-dimethyl-2-phenyl-N-[2-(4-trifluoromethyl-phenyl)-ethyl]-malonamide | N,N-Dimethyl-2-phenyl-malonamic acid (WO000009481) and (2-Chloro-5-methoxy-phenyl)-[2-(4-trifluoromethyl-phenyl)-ethyl]-amine (intermediate 20) | 519.2 |
| 55 | 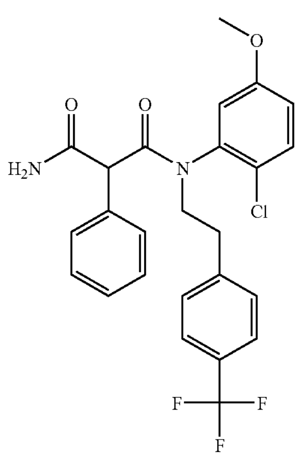 | 490.9 | N-(2-Chloro-5-methoxy-phenyl)-2-phenyl-N-[2-(4-trifluoromethyl-phenyl)-ethyl]-malonamide | 2-Phenyl-malonamic acid (JACS 1955, 77, 4849-51) and (2-Chloro-5-methoxy-phenyl)-[2-(4-trifluoromethyl-phenyl)-ethyl]-amine (intermediate 20) | 491.1 |

TABLE 3-continued

| No | structure | MW | name | starting material | MW MH+ found |
|---|---|---|---|---|---|
| 56 | 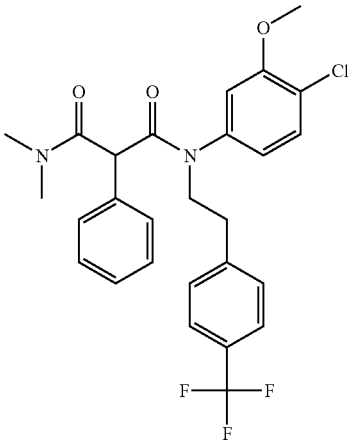 | 519.0 | N-(4-Chloro-3-methoxy-phenyl)-N',N'-dimethyl-2-phenyl-N-[2-(4-trifluoromethyl-phenyl)-ethyl]-malonamide | N,N-Dimethyl-2-phenyl-malonamic acid (WO000009481) and (4-Chloro-3-methoxy-phenyl)-[2-(4-trifluoromethyl-phenyl)-ethyl]-amine (intermediate 21) | 519.2 |
| 57 | 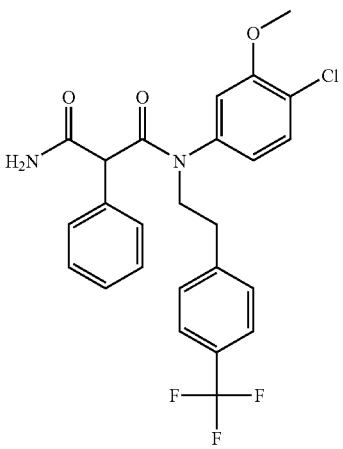 | 490.9 | N-(4-Chloro-3-methoxy-phenyl)-2-phenyl-N-[2-(4-trifluoromethyl-phenyl)-ethyl]-malonamide | 2-Phenyl-malonamic acid (JACS 1955, 77, 4849-51) and (4-Chloro-3-methoxy-phenyl)-[2-(4-trifluoromethyl-phenyl)-ethyl]-amine (intermediate 21) | 491.1 |
| 58 | 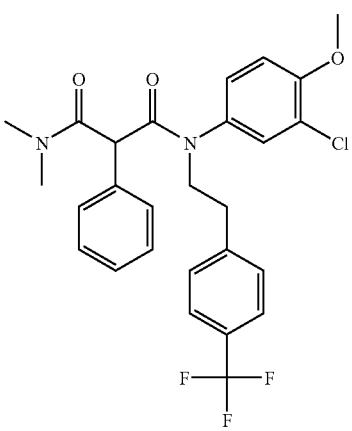 | 519.0 | N-(3-Chloro-4-methoxy-phenyl)-N',N'-dimethyl-2-phenyl-N-[2-(4-trifluoromethyl-phenyl)-ethyl]-malonamide | N,N-Dimethyl-2-phenyl-malonamic acid (WO000009481) and (3-Chloro-4-methoxy-phenyl)-[2-(4-trifluoromethyl-phenyl)-ethyl]-amine (intermediate 22) | 519.2 |

TABLE 3-continued

| No | structure | MW | name | starting material | MW MH+ found |
|---|---|---|---|---|---|
| 59 | 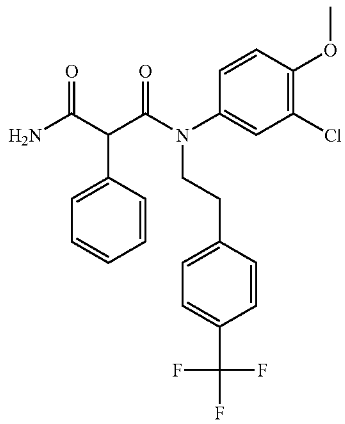 | 490.9 | N-(3-Chloro-4-methoxy-phenyl)-2-phenyl-N-[2-(4-trifluoromethyl-phenyl)-ethyl]-malonamide | 2-Phenyl-malonamic acid (JACS 1955, 77, 4849-51) and (3-Chloro-4-methoxy-phenyl)-[2-(4-trifluoromethyl-phenyl)-ethyl]-amine (intermediate 22) | 491.1 |
| 60 | 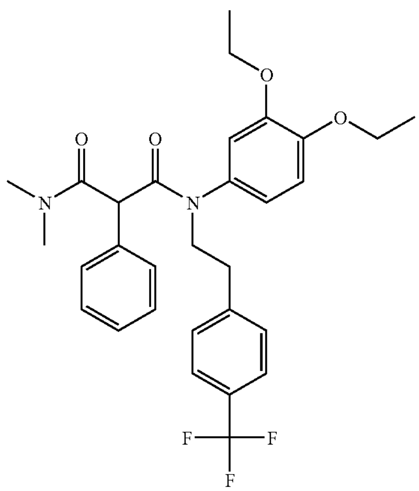 | 542.6 | N-(3,4-Diethoxy-phenyl)-N',N'-dimethyl-2-phenyl-N-[2-(4-trifluoromethyl-phenyl)-ethyl]-malonamide | N,N-Dimethyl-2-phenyl-malonamic acid (WO000009481) and (3,4-Diethoxy-phenyl)-[2-(4-trifluoromethyl-phenyl)-ethyl-amine (intermediate 23) | 543.2 |
| 61 | 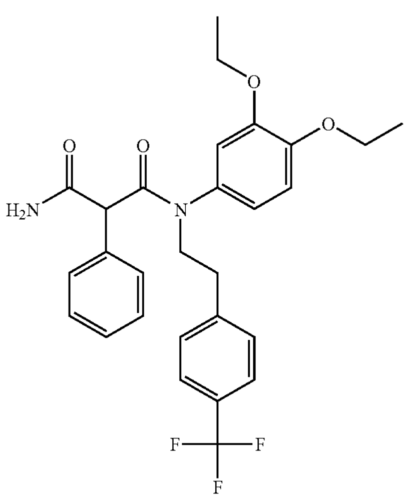 | 514.5 | N-(3,4-Diethoxy-phenyl)-2-phenyl-N-[2-(4-trifluoromethyl-phenyl)-ethyl]-malonmide | 2-Phenyl-malonamic acid (JACS 1955, 77, 4849-51) and (3,4-Diethoxy-phenyl)-[2-(4-trifluoromethyl-phenyl)-ethyl]-amine (intermediate 23) | 515.2 |

TABLE 3-continued

| No | structure | MW | name | starting material | MW MH+ found |
|---|---|---|---|---|---|
| 62 | 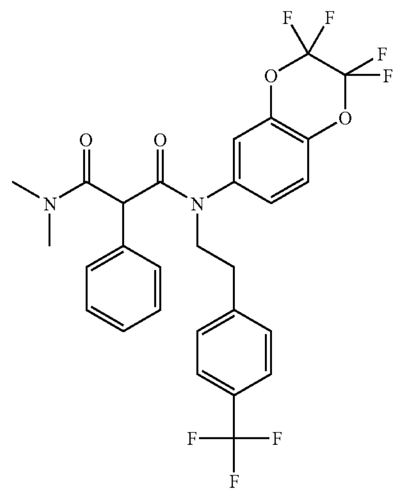 | 584.5 | N,N-Dimethyl-2-phenyl-N'-(2,2,3,3-tetrafluoro-2,3-dihydro-benzo[1,4]dioxin-6-yl)-N'-[2-(4-trifluoromethyl-phenyl)-ethyl]-malonamide | N,N-Dimethyl-2-phenyl-malonamic acid WO000009481 and (2,2,3,3-Tetrafluoro-2,3-dihydro-benzo[1,4]dioxin-6-yl)-[2-(4-trifluoromethyl-phenyl)-ethyl]-amine (intermediate 24) | 585.2 |

EXAMPLE 63

N-(3,4-Dimethoxy-phenyl)-2,N',N'-trimethyl-2-phenyl-N-[2-(4-trifluoromethyl-phenyl)-ethyl]-malonamide

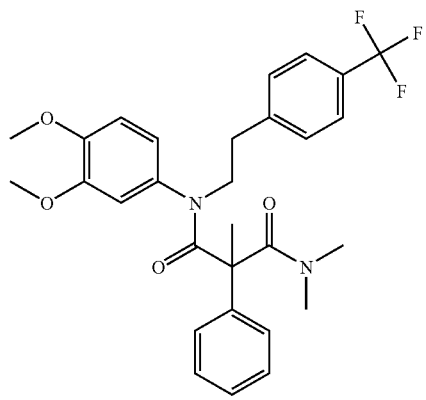

a) Step 1:

N-(3,4-Dimethoxy-phenyl)-2-methyl-2-phenyl-N-[2-(4-trifluoromethyl-phenyl)-ethyl]-malonamic acid ethyl ester A mixture of 97.5 mg (0.3 mmol) (3,4-dimethoxy-phenyl)-[2-(4-trifluoromethyl-phenyl)-ethyl]-amine (intermediate 1), 101 mg (0.45 mmol) 2-chlorocarbonyl-2-phenyl-propionic acid ethyl ester (Journal of Organic Chemistry (1959), 24 109-10) and 121 mg (1.2 mmol) triethylamine 15 mL DCM was stirred for 16 h at room temperature. The mixture was evaporated and purified by preparative HPLC on reversed phase eluting with a gradient formed from acetonitrile, water and formic acid, the product containing fractions were evaporated to yield 71.5 mg (45%) of the title compound. MS(m/e): 530.2 (MH+).

b) Step 2:

A mixture of 42 mg (0.08 mmol) N-(3,4-dimethoxy-phenyl)-2-methyl-2-phenyl-N-[2-(4-trifluoromethyl-phenyl)-ethyl]-malonamic acid ethyl ester and NaOH/KOH aq. in ethanol was heated to 80° C. and extracted with ethyl acetate, the combined organic layers were dried with MgSO4 and concentrated. DMF and dimethylamine in ethanol (33%) was added and the mixture was stirred for 16 h at room temperature and evaporated. The residue was purified by preparative HPLC on reversed phase eluting with a gradient formed from acetonitrile, water and formic acid, the product containing fractions were evaporated to yield 23.6 mg (56%) of the title compound. MS(m/e): 529.2 (MH+).

EXAMPLE 64

N-[2-(3,4-Dimethoxy-phenyl)-ethyl]-N-(4-methoxy-phenyl)-2,N',N'-trimethyl-2-phenyl-malonamide

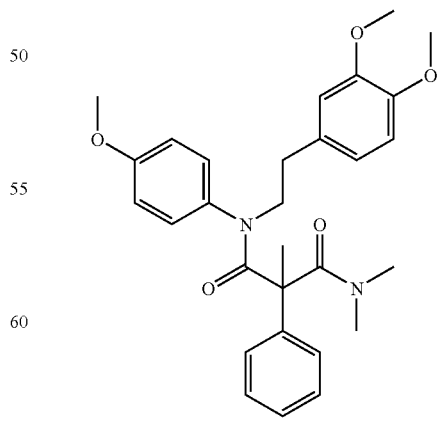

In analogy to the procedure described for the synthesis of N-(3,4-Dimethoxy-phenyl)-2,N',N'-trimethyl-2-phenyl-N-

[2-(4-trifluoromethyl-phenyl)-ethyl]-malonamide (example 63) the title compound was prepared from [2-(3,4-Dimethoxy-phenyl)-ethyl]-(4-methoxy-phenyl)-amine (intermediate 2), 2-Chlorocarbonyl-2-phenyl-propionic acid ethyl ester (Journal of Organic Chemistry (1959), 24 109-10) and, after saponification, dimethylamine. MS(m/e): 491.2 (MH+).

The invention claimed is:

1. A compound of formula I

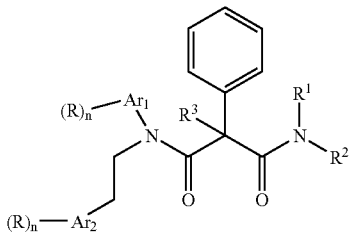

I wherein

Ar$_1$ and Ar$_2$ are each independently unsubstituted or substituted aryl or heteroaryl;

R$^1$ and R$^2$ are each independently hydrogen, lower alkyl, lower alkyl substituted by halogen, —(CH$_2$)$_o$—O-lower alkyl, —(CH$_2$)$_o$—N-(lower alkyl)$_2$, (CH$_2$)$_p$-cycloalkyl, (CH$_2$)$_p$-heterocycloalkyl, (CH$_2$)$_p$-aryl, or (CH$_2$)$_p$-heteroaryl, wherein cycloalkyl, heterocycloalkyl, aryl, and heteroaryl are optionally substituted by R, or R$^1$ and R$^2$ together with the N-atom to which they are attached form a heterocyclic ring, optionally containing further ring-heteroatoms selected from N, O and S, which ring is optionally substituted by R;

R is halogen, lower alkyl, lower alkyl substituted by halogen, lower alkoxy or lower alkoxy substituted by halogen;

R$^3$ is hydrogen or lower alkyl;

n is 0, 1, 2, 3 or 4;

o is 1, 2 or 3; and p is 0, 1 or 2;

or a pharmaceutically suitable acid addition salt, optically pure enantiomer, racemate or diastereomeric mixture thereof.

2. A compound of claim 1 having formula I-1

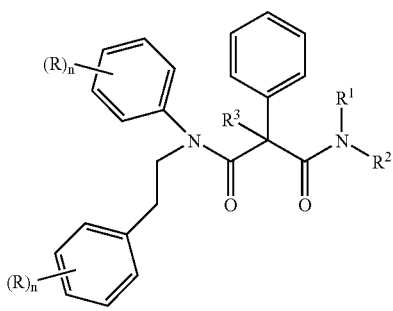

I-1 wherein

R$^1$ and R$^2$ are each independently hydrogen, lower alkyl, lower alkyl substituted by halogen, —(CH$_2$)$_o$—O-lower alkyl, —(CH$_2$)$_o$—N-(lower alkyl)$_2$, (CH$_2$)$_p$-cycloalkyl, (CH$_2$)$_p$-heterocycloalkyl, (CH$_2$)$_p$-aryl, or (CH$_2$)$_p$-heteroaryl, wherein cycloalkyl, heterocycloalkyl, aryl, and heteroaryl are optionally substituted by R, or R$^1$ and R$^2$ together with the N-atom to which they are attached form a heterocyclic ring, optionally containing further ring-heteroatoms selected from N, O and S, which ring is optionally substituted by R;

R is halogen, lower alkyl, lower alkyl substituted by halogen, lower alkoxy or lower alkoxy substituted by halogen;

R$^3$ is hydrogen or lower alkyl;

n is 0, 1, 2, 3 or 4;

o is 1, 2 or 3; and p is 0, 1 or 2;

or a pharmaceutically suitable acid addition salt, optically pure enantiomer, racemate or diastereomeric mixture thereof.

3. A compound of claim 2 having formula I-2

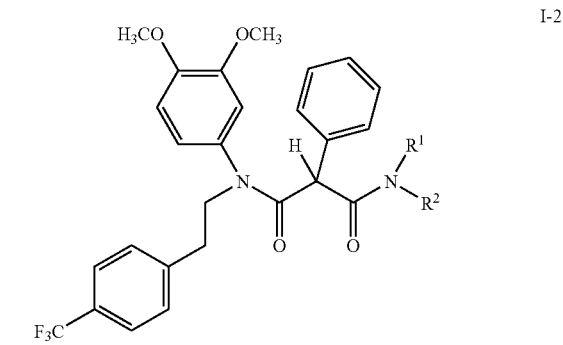

I-2 wherein

R$^1$ and R$^2$ are each independently hydrogen, lower alkyl, lower alkyl substituted by halogen, —(CH$_2$)$_o$—O-lower alkyl, —(CH$_2$)$_o$—N-(lower alkyl)$_2$, (CH$_2$)$_p$-cycloalkyl, (CH$_2$)$_p$-heterocycloalkyl, (CH$_2$)$_p$-aryl, or (CH$_2$)$_p$-heteroaryl, wherein cycloalkyl, heterocycloalkyl, aryl, and heteroaryl are optionally substituted by R, or R$^1$ and R$^2$ together with the N-atom to which they are attached form a heterocyclic ring, optionally containing further ring-heteroatoms selected from N, O and S, which ring is optionally substituted by R;

R is halogen, lower alkyl, lower alkyl substituted by halogen, lower alkoxy or lower alkoxy substituted by halogen;

o is 1, 2 or 3; and p is 0, 1 or 2;

or a pharmaceutically suitable acid addition salt, optically pure enantiomer, racemate or diastereomeric mixture thereof.

4. A compound of claim 2 selected from the group consisting of

N-(4-Chloro-3-methoxy-phenyl)-N',N'-dimethyl-2-phenyl-N-[2-(4-trifluoromethyl-phenyl)-ethyl]-malonamide and N-(3-Chloro-4-methoxy-phenyl)-N',N'-dimethyl-2-phenyl-N-[2-(4-trifluoromethyl-phenyl)-ethyl]-malonamide.

5. A compound of claim 3, wherein one of R$^1$ or R$^2$ is hydrogen and the other is lower alkyl.

6. A compound of claim 5 selected from the group consisting of

N-(3,4-dimethoxy-phenyl)-N'-methyl-2-phenyl-N-[2-(4-trifluoromethyl-phenyl)-ethyl]-malonamide N-butyl-N'-(3,4-dimethoxy-phenyl)-2-phenyl-N'-[2-(4-trifluoromethyl-phenyl)-ethyl]-malonamide N-(3,4-dimethoxy-phenyl)-N'-ethyl-2-phenyl-N-[2-(4-trifluoromethyl-phenyl)-ethyl]-malonamide and N-(3,4-dimethoxy-phenyl)-2-phenyl-N'-propyl-N-[2-(4-trifluoromethyl-phenyl)-ethyl]-malonamide.

7. A compound of claim 3, wherein one of $R^1$ or $R^2$ is hydrogen and the other is —$(CH_2)_o$—O-lower alkyl.

8. A compound of claim 7 which compound is
N-(3,4-dimethoxy-phenyl)-N'-(2-methoxy-ethyl)-2-phenyl-N-[2-(4-trifluoromethyl-phenyl)-ethyl]-malonamide.

9. A compound of claim 3, wherein one of $R^1$ or $R^2$ is hydrogen and the other is phenyl substituted by halogen.

10. A compound of claim 9, which compound is
N-(3,4-dimethoxy-phenyl)-N'-(4-fluoro-phenyl)-2-phenyl-N-[2-(4-trifluoromethyl-phenyl)-ethyl]-malonamide.

11. A compound of claim 3, wherein $R^1$ and $R^2$ are both hydrogen.

12. A compound of claim 11, which compound is
N-(3,4-dimethoxy-phenyl)-2-phenyl-N-[2-(4-trifluoromethyl-phenyl)-ethyl]-malonamide.

13. A compound of claim 3, wherein $R^2$ is unsubstituted or substituted $(CH_2)_p$-aryl.

14. A compound of claim 13, selected from the group consisting of
N-(3,4-dimethoxy-phenyl)-N'-(4-methyl-benzyl)-2-phenyl-N-[2-(4-trifluoromethyl-phenyl)-ethyl]-malonamide N-(3,4-dimethoxy-phenyl)-N'-methyl-N'-phenethyl-2-phenyl-N-[2-(4-trifluoromethyl-phenyl)-ethyl]-malonamide and N-benzyl-N'-(3,4-dimethoxy-phenyl)-N-methyl-2-phenyl-N'-[2-(4-trifluoromethyl-phenyl)-ethyl]-malonamide.

15. A compound of claim 3, wherein one of $R^1$ or $R^2$ is hydrogen and the other is unsubstituted or substituted $(CH_2)_p$-cycloalkyl.

16. A compound of claim 15, selected from the group consisting of
N-cyclopropyl-N'-(3,4-dimethoxy-phenyl)-2-phenyl-N'-[2-(4-trifluoromethyl-phenyl)-ethyl]-malonamide and N-cyclopropylmethyl-N'-(3,4-dimethoxy-phenyl)-2-phenyl-N'-[2-(4-trifluoromethyl-phenyl)-ethyl]-malonamide.

17. A compound of claim 3, wherein one of $R^1$ or $R^2$ is hydrogen and the other is lower alkyl substituted by halogen.

18. A compound of claim 17, which compound is
N-(2,2-difluoro-ethyl)-N'-(3,4-dimethoxy-phenyl)-2-phenyl-N'-[2-(4-trifluoromethyl-phenyl)-ethyl]-malonamide.

19. A compound of formula I-2 according to claim 3, wherein one of $R^1$ or $R^2$ is hydrogen and the other is unsubstituted or substituted $(CH_2)_p$-heteroaryl.

20. A compound of claim 19, selected from the group consisting of
N-(3,4-dimethoxy-phenyl)-2-phenyl-N'-pyridin-3-yl-N-[2-(4-trifluoromethyl-phenyl)-ethyl]-malonamide and N-(3,4-dimethoxy-phenyl)-2-phenyl-N'-pyridin-3-ylmethyl-N-[2-(4-trifluoromethyl-phenyl)-ethyl]-malonamide.

21. A compound of claim 3, wherein one of $R^1$ or $R^2$ is hydrogen and the other is unsubstituted or substituted $(CH_2)_p$-heterocycloalkyl.

22. A compound of claim 21, which compound is
N-(3,4-dimethoxy-phenyl)-2-phenyl-N'-(tetrahydro-pyran-4-yl)-N-[2-(4-trifluoromethyl-phenyl)-ethyl]-malonamide.

23. A pharmaceutical composition comprising a therapeutically effective amount of a compound of formula I

I wherein $Ar_1$ and $Ar_2$ are each independently unsubstituted or substituted aryl or heteroaryl;

$R^1$ and $R^2$ are each independently hydrogen, lower alkyl, lower alkyl substituted by halogen, —$(CH_2)_o$—O-lower alkyl, —$(CH_2)_o$—N-(lower alkyl)$_2$, $(CH_2)_p$-cycloalkyl, $(CH_2)_p$-heterocycloalkyl, $(CH_2)_p$-aryl, or $(CH_2)_p$-heteroaryl, wherein cycloalkyl, heterocycloalkyl, aryl, and heteroaryl are optionally substituted by R, or $R^1$ and $R^2$ together with the N-atom to which they are attached form a heterocyclic ring, optionally containing further ring-heteroatoms selected from N, O and S, which ring is optionally substituted by R;

R is halogen, lower alkyl, lower alkyl substituted by halogen, lower alkoxy or lower alkoxy substituted by halogen;

$R^3$ is hydrogen or lower alkyl;

n is 0, 1, 2, 3 or 4;

o is 1, 2 or 3; and p is 0, 1 or 2;

or a pharmaceutically suitable acid addition salt, optically pure enantiomer, racemate or diastereomeric mixture thereof and a pharmaceutically acceptable carrier.

* * * * *